United States Patent
Oldham et al.

(10) Patent No.: US 6,645,491 B1
(45) Date of Patent: Nov. 11, 2003

(54) METHOD FOR TREATING INFLAMMATORY CONDITIONS USING AN ANTIBODY TO MIP-3α

(75) Inventors: Elizabeth R. Oldham, Mountain View, CA (US); Bernhard Homey, Palo Alto, CA (US); Marie Caroline Dieu-Nosjean, Rueil-Malmaison (FR); Christophe Caux, Bressolles (FR); Albert Zlotnik, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/503,219

(22) Filed: Feb. 2, 2000

Related U.S. Application Data

(60) Provisional application No. 60/118,335, filed on Feb. 3, 1999.

(51) Int. Cl.$^7$ .............................................. A61K 39/395
(52) U.S. Cl. ............................... 424/139.1; 424/130.1; 424/158.1
(58) Field of Search .......................... 435/7.1; 530/350, 530/388.1, 388.15, 388.23; 424/85.1, 139.1, 130.1, 158.1

(56) References Cited

U.S. PATENT DOCUMENTS

| | | | |
|---|---|---|---|
| 5,504,003 A | 4/1996 | Li et al. | ................... 435/240.2 |
| 5,981,230 A | 11/1999 | Li et al. | |
| 6,057,426 A | * 5/2000 | Lesslauer et al. | ............ 530/351 |

FOREIGN PATENT DOCUMENTS

| | | |
|---|---|---|
| WO | WO 96/16979 | 6/1996 |
| WO | WO 98/01557 | 1/1998 |
| WO | WO 99/20759 | 4/1999 |
| WO | WO 00/09151 | 2/2000 |

OTHER PUBLICATIONS

Christine A. Power, et al., *J. Exp. Med.*, 186(6):825–835, Sep. 15, 1997. "Cloning and Characterization of a Specific Receptor for the Novel CC Chemokine MIP-3 α from Lung Dendritic Cells".
Sunil K. Ahuja, et al., *Immunol. Today* 15:281–287, 1994. "Chemokine Receptors and Molecular Mimicry".
Ghalig Alkatib, et al., *Science* 272:1955–1958, Jun. 28, 1996. "CC CKR5: A RANTES, MIP-1α, MIP-1β Receptor as a Fusion Cofactor for Macorphage-Tropic HIV-1".
Masataka Baba, et al., *J. Biological Chemistry*, 272(23):14893–14898, Jun. 6, 1997. "Identification of CCR6, the Specific Receptor for a Novel Lymphocyte-directed CC Chemokine LARC".
Kevin B. Bacon, et al., *Int. Arch. Allergy Immunol.* 109:97–109, 1996. "Chemokines as Mediators of Allergic Inflammation".
Michael Balter, *Science* 272:1740, Jun. 21, 1996. "A Second Coreceptor for HIV in Early Stages of Infection".

Ian Clark-Lewis, et al., *J. Leukoc. Biol.* 57:703–711, 1995. "Structure-Activity Relationships of Chemokines".
HongKui Deng, et al., *Nature* 381:661–666, Jun. 20, 1996. "Identification of a Major Co-Receptor for Primary Isolates of HIV-1".
Tatjana Dragic, et al., *Nature* 381:667–673, Jun. 20, 1996. "HIV Entry into CD4+ Cells is Mediated by the Chemokine Receptor CC-CKR-5".
David P. Gearing, et al., *EMBO Journal*, 8(12):367–3676, 1989. "Expression cloning of a receptor for human granulocyte-macrophage colony stimulating factor".
David R. Greaves, et al., *J. Exp. Med.*, 186(6):837–844, Sep. 15, 1997. "CCR6, a CC Chemokine Receptor that Interacts with Macrophage Iflammatory Protein 3α and Is Highly Expressed in Human Dendritic Cells".
Angela M. Gronenborn, et al., *Prot. Engg.* 4:263–269, 1991. "Modeling the Three-Dimensional Structure of the Monocyte Chemo-Attractant and Activating Protein MCAF/MCP-1 on the Basis of the Solution Structure ofInterleukin-8".
Kunio Hieshima, et al., *J. Biological Chemistry*, 272(9):5846–5853, Feb. 28, 1997. "Molecular Cloning of a Novel Human CC Chemokine Liver and Activation-regulated Chemokine (LARC) Expressed in Liver".
R. Horuk, et al., *J. Leukoc. Biol.* 59:29–38, Jan. 1996. "The Duffy Antigen Receptor for Chemokines: Structural Analysis and Expression in the Brain".
Richard Horuk, *TIPS* 15:159–165, May 1994. "Molecular Properties of the Chemokine Receptor Family".
Richard Horuk, *Immunol. Today* 15:169–174, 1994. "The Interleukin-8-Receptor Family: From Chemokines to Malaria".
Toshi Imai, et al. *J. Biol. Chem.*, 272(33):15036–15042, Jun. 6, 1997. "The T Cell-directed CC Chemokines TARC Is a Highly Specific Biological Ligand for CC Chemokine Receptor 4".
David J. Kelvin, et al., *J. of Leukocyte Biology*, 54:604–612, Dec. 1993. "Chemokines and serpentines: the molecular biology of chemokine receptors".
Fang Liao, et al., *Biochem. Biophys. Res. Commun.*, 236:212–217, 1997. "STRL22 Is a Receptor for the CC Chemokine MIP-3α".
Fang Liao, et al., *J. Immunology*, 162:186–194, 1999. "CC-Chemokine Receptor 6 Is Expressed on Diverse Memory Subsets of T Cells and Determines Responsiveness to Macrophage Inflammatory Protein-3α".
Patricia J. Lodi, et al., *Science* 263:1762–1767, Mar. 25, 1994. "High-Resolution Structure of the β Chemokine hMIP-1β by Multidimensional NMR".

(List continued on next page.)

*Primary Examiner*—Prema Mertz
(74) *Attorney, Agent, or Firm*—Edwin P. Ching; Sandy Zaradic

(57) ABSTRACT

Agonists or antagonists of MIP-3α, and various methods of use in dermatological and related applications are provided. In particular, the method makes use of fact that the MIP-3α chemokine is specifically capable of inducing migration of a skin cell subset.

22 Claims, No Drawings

OTHER PUBLICATIONS

Adriano Marchese, et al., *Genomics* 23:609–618, 1994. "Cloning of Human Genes Encoding Novel G Protein-Coupled Receptors".

A. Marchese, et al., *GenBank*, Accession No. U13667, L35537, Apr. 1, 1995. Definition: Human G protein–coupled receptor (GPR2) gene, partial cds.

M. Marra, et al., *GenBank*, Accession No. AA930619, Apr. 23, 1998. Definition: vy67b03.r1 Stratagene mouse macrophage (#937306) Mus musculus cDNA clone Image:1096356 5' similar to SW:GPR2–Human P46092 Probable G Protein–Coupled Receptor GPR2.;, mRNA sequence.

M. Marra, et al., *GenBank*, Accession No. AA871520, Mar. 16, 1998. Definition: vq36e01.r1 Barstead bowel MPLRB9 Mus musculus cDNA clone Image:1311245 5' similar to SW:GPR2–Human P46092 Probable G Protein–Coupled Receptor GPR2. ;, mRNA sequence.

M. Mama, et al,, *GenBank*, Accession No. AA023970, Jan. 21, 1997. Definition: mh95f08.r1 Soares mouse placenta 4NbMP13.5 14.5 Mus musculus cDNA clone Image:458727 5' similar to SW:GPR2–Human P46092 Probable G Protein–Coupled Receptor GPR2. [1];, mRNA sequence.

Kouji Matsushima, et al., *Cytokine* 1:2–13, Nov. 1989. "Interleukin 8 and MCAF: Novel Inflammatory Cytokines Inducible byu IL 1 and TNF".

Catherine J. McMahan, et al., *EMBO Journal*, 10(10):2821–2832, 1991. "A Novel IL–1 receptor, cloned from B cells by mammalian expression, is expressed in many cell types".

Michael D. Miller, et al., *Proc. Natl. Acad. Sci.* 89:2950–2954, 1992. "The Human Cytokines I–309 is a Monocyte Chemoattractant".

Joost J. Oppenheim, et al., *Ann. Rev. Immunol.* 9:617–648, 1991. "Properties of the Novel Proinflammatory Supergene 'Intercrine' Cytokine Family".

Paul Proost, et al., *J. Leukoc. Biol.* 59:67–74, Jan. 1996. "Human Monocyte Chemoatactic Proteins–2 and –3: Structural and Functional Comparison with MCP–1".

Carol J. Rossi, et al., *J. Immunology*, 158(3):1033–1036, Feb. 1997. "Indentification Through Bioinformatics of Two New Macrophage Proinflammatory Human Chemokines MIP03α, MIP–3β[1,2]".

Michel Samson, et al., *Biochem.* 35:3362–3367, 1996. "Molecular Cloning and Functional Expression of a New Human CC–Chemokine Receptor Gene".

Roger A. Sayle and E. James Milner–White, *TIBS*, 20:374–376, Sep. 1995. "RASMOL: biomolecular graphics for all".

Thomas J. Schall, in *The Cytokine Handbook*, 2nd ed., Academic Press Ltd., NY, pp. 419–460, 1994. "The Chemokines".

Thomas J. Schall and Kevin B. Bacon, *Curr. Opin. Immunol.* 6:865–873, 1994. "Chemokines, Leukocyte Trafficking, and Inflammation".

Thomas J. Schall, *Cytokine* 3:165–183, May 1991. "Biology of the RANTES/SIS Cytokine Family".

Thomas J. Schall, et al., in *The Chemokines*, Plenum Press, NY, pp. 29–37, 1993. "Receptor/Ligand Interactions in the C–C Chemokine Family".

Mark Y. Stoeckle, et al., *The New Biologist* 2:313–323, Apr. 1990. "Two Burgeoning Families of Platelet Factor 4–Related Proteins: Mediators of the Inflammatory Response".

Robert M. Strieter and Steven L. Kunkel, *J. Inv. Med.* 42:640–651, Dec. 1994. "Acute Lung Injury: The Role of Cytokines in the Elicitation of Neutrophils".

Robert M. Strieter, et al., *J. Leukoc. Bio.* 57:752–762, May 1995. "Role of C–X–C Chemokines as Regulators of Angiogenesis in Lung Cancer".

Angus W. Thompson, Ed., *The Cytokine Handbook*, 2nd ed., The Academic Press Inc.: San Diego, CA, 1994.

Alain P. Vicari, et al., *J. Allergy Clin. Immun.*, 99(1) part 2:S246, Abstract 1003, Jan. 1997. "TECK: a novel CC Chemokine associated with T–cell development".

Alain P. Vicari, et al., *Immunity*, 7:291–301, Aug. 1997. "TECK: a novel CC Chemokines Specifically Expressed by Thymic Dendritic Cells and Potentially Involved in T–cell development".

Ulrich O. Wenzel, et al., *Am. J. Kidney Diseases* 26:982–994, Dec. 1995. "Chemokines and Renal Disease".

Ryu Yoshida, et al., *J. Biological Chemistry*, 272(21):13803–13809, May 23, 1997. "Molecular Cloning of a Novel Human CC Chemokine EBI1–ligand Chemokine That Is a Specific Functional Ligand for EBI1, CCR7".

Osamu Yoshie, et al., *J. Leukocyte Biology*, 62(5):634–644, Nov. 1997. "Novel lymphocyte–specific CC chemokines and their receptors".

Angel Zaballos, et al., *Biochem Biophys. Res. Comm.*, 227(3):846–853, Oct. 1996. "Molecular Cloning and RNA Expression of Two New Human Chemokine Receptor–like Genes".

\* cited by examiner

SEQUENCE LISTING

```
<160> NUMBER OF SEQ ID NOS: 8

<210> SEQ ID NO 1
<211> LENGTH: 291
<212> TYPE: DNA
<213> ORGANISM: Homo sapiens
<220> FEATURE:
<221> NAME/KEY: CDS
<222> LOCATION: (1)..(288)
<223> OTHER INFORMATION:

<400> SEQUENCE: 1 atg tgc tgt acc aag agt ttg ctc ctg gct gct ttg atg tca gtg ctg      48
Met Cys Cys Thr Lys Ser Leu Leu Leu Ala Ala Leu Met Ser Val Leu
1               5                   10                  15 cta ctc cac ctc tgc ggc gaa tca gaa gca gca agc aac ttt gac tgc      96
Leu Leu His Leu Cys Gly Glu Ser Glu Ala Ala Ser Asn Phe Asp Cys
            20                  25                  30 tgt ctt gga tac aca gac cgt att ctt cat cct aaa ttt att gtg ggc     144
Cys Leu Gly Tyr Thr Asp Arg Ile Leu His Pro Lys Phe Ile Val Gly
        35                  40                  45 ttc aca cgg cag ctg gcc aat gaa ggc tgt gac atc aat gct atc atc     192
Phe Thr Arg Gln Leu Ala Asn Glu Gly Cys Asp Ile Asn Ala Ile Ile
    50                  55                  60 ttt cac aca aag aaa aag ttg tct gtg tgc gca aat cca aaa cag act     240
Phe His Thr Lys Lys Lys Leu Ser Val Cys Ala Asn Pro Lys Gln Thr
65                  70                  75                  80 tgg gtg aaa tat att gtg cgt ctc ctc agt aaa aaa gtc aag aac atg     288
Trp Val Lys Tyr Ile Val Arg Leu Leu Ser Lys Lys Val Lys Asn Met
                85                  90                  95 taa                                                                  291

<210> SEQ ID NO 2
<211> LENGTH: 96
<212> TYPE: PRT
<213> ORGANISM: Homo sapiens

<400> SEQUENCE: 2
```

```
Met Cys Cys Thr Lys Ser Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
                35                  40                  45

Phe Thr Arg Gln Leu Ala Asn Glu Gly Cys Asp Ile Asn Ala Ile Ile
            50                  55                  60

Phe His Thr Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95
```

<210> SEQ ID NO 3
<211> LENGTH: 291
<212> TYPE: DNA
<213> ORGANISM: Mus musculus
<220> FEATURE:
<221> NAME/KEY: CDS
<222> LOCATION: (1)..(288)
<223> OTHER INFORMATION:

<400> SEQUENCE: 3

```
atg gcc tgc ggt ggc aag cgt ctg ctc ttc ctt gct ttg gca tgg gta        48
Met Ala Cys Gly Gly Lys Arg Leu Leu Phe Leu Ala Leu Ala Trp Val
1               5                   10                  15 ctg ctg gct cac ctc tgc agc cag gca gaa gca agc aac tac gac tgt        96
Leu Leu Ala His Leu Cys Ser Gln Ala Glu Ala Ser Asn Tyr Asp Cys
            20                  25                  30 tgc ctc tcg tac ata cag acg cca ctt cct tcc aga gct att gtg ggt       144
Cys Leu Ser Tyr Ile Gln Thr Pro Leu Pro Ser Arg Ala Ile Val Gly
                35                  40                  45 ttc aca aga cag atg gcc gat gaa gct tgt gac att aat gct atc atc       192
Phe Thr Arg Gln Met Ala Asp Glu Ala Cys Asp Ile Asn Ala Ile Ile
            50                  55                  60 ttt cac acg aag aaa aga aaa tct gtg tgc gct gat cca aag cag aac       240
Phe His Thr Lys Lys Arg Lys Ser Val Cys Ala Asp Pro Lys Gln Asn
65                  70                  75                  80 tgg gtg aaa agg gct gtg aac ctc ctc agc cta aga gtc aag aag atg       288
Trp Val Lys Arg Ala Val Asn Leu Leu Ser Leu Arg Val Lys Lys Met
                85                  90                  95 taa                                                                   291
```

<210> SEQ ID NO 4
<211> LENGTH: 96
<212> TYPE: PRT
<213> ORGANISM: Mus musculus

<400> SEQUENCE: 4

```
Met Ala Cys Gly Gly Lys Arg Leu Leu Phe Leu Ala Leu Ala Trp Val
1               5                   10                  15

Leu Leu Ala His Leu Cys Ser Gln Ala Glu Ala Ser Asn Tyr Asp Cys
            20                  25                  30

Cys Leu Ser Tyr Ile Gln Thr Pro Leu Pro Ser Arg Ala Ile Val Gly
                35                  40                  45

Phe Thr Arg Gln Met Ala Asp Glu Ala Cys Asp Ile Asn Ala Ile Ile
            50                  55                  60

Phe His Thr Lys Lys Arg Lys Ser Val Cys Ala Asp Pro Lys Gln Asn
65                  70                  75                  80
```

-continued

```
Trp Val Lys Arg Ala Val Asn Leu Leu Ser Leu Arg Val Lys Lys Met
                85                  90                  95

<210> SEQ ID NO 5
<211> LENGTH: 291
<212> TYPE: DNA
<213> ORGANISM: Rattus rattus
<220> FEATURE:
<221> NAME/KEY: CDS
<222> LOCATION: (1)..(288)
<223> OTHER INFORMATION:

<400> SEQUENCE: 5 atg gcc tgc aag cat ctg ccc ttc ctg gct ttg gcg ggg gta ctg ctg      48
Met Ala Cys Lys His Leu Pro Phe Leu Ala Leu Ala Gly Val Leu Leu
1               5                   10                  15 gct tac ctc tgc agc cag tca gaa gca gca agc aac ttt gac tgc tgc      96
Ala Tyr Leu Cys Ser Gln Ser Glu Ala Ala Ser Asn Phe Asp Cys Cys
                20                  25                  30 ctc acg tac aca aag aac gtg tat cat cat gcg aga aat ttt gtg ggt     144
Leu Thr Tyr Thr Lys Asn Val Tyr His His Ala Arg Asn Phe Val Gly
            35                  40                  45 ttc aca aca cag atg gcc gac gaa gct tgt gac att aat gct atc atc     192
Phe Thr Thr Gln Met Ala Asp Glu Ala Cys Asp Ile Asn Ala Ile Ile
        50                  55                  60 ttt cac ctg aag tcg aaa aga tcc gtg tgc gct gac cca aag cag atc     240
Phe His Leu Lys Ser Lys Arg Ser Val Cys Ala Asp Pro Lys Gln Ile
65                  70                  75                  80 tgg gtg aaa agg att ttg cac ctc ctc agc cta aga acc aag aag atg     288
Trp Val Lys Arg Ile Leu His Leu Leu Ser Leu Arg Thr Lys Lys Met
                85                  90                  95 taa                                                                  291

<210> SEQ ID NO 6
<211> LENGTH: 96
<212> TYPE: PRT
<213> ORGANISM: Rattus rattus

<400> SEQUENCE: 6

Met Ala Cys Lys His Leu Pro Phe Leu Ala Leu Ala Gly Val Leu Leu
1               5                   10                  15

Ala Tyr Leu Cys Ser Gln Ser Glu Ala Ala Ser Asn Phe Asp Cys Cys
                20                  25                  30

Leu Thr Tyr Thr Lys Asn Val Tyr His His Ala Arg Asn Phe Val Gly
            35                  40                  45

Phe Thr Thr Gln Met Ala Asp Glu Ala Cys Asp Ile Asn Ala Ile Ile
        50                  55                  60

Phe His Leu Lys Ser Lys Arg Ser Val Cys Ala Asp Pro Lys Gln Ile
65                  70                  75                  80

Trp Val Lys Arg Ile Leu His Leu Leu Ser Leu Arg Thr Lys Lys Met
                85                  90                  95

<210> SEQ ID NO 7
<211> LENGTH: 1098
<212> TYPE: DNA
<213> ORGANISM: Homo sapiens
<220> FEATURE:
<221> NAME/KEY: CDS
<222> LOCATION: (1)..(1098)
<223> OTHER INFORMATION:
<220> FEATURE:
<221> NAME/KEY: misc_feature
```

<222> LOCATION: (579)..(579)
<223> OTHER INFORMATION: unknown nucleotide

<400> SEQUENCE: 7

```
atg ttt tcg act cca gtg aag att att ttg tgt cag tca ata ctt cat      48
Met Phe Ser Thr Pro Val Lys Ile Ile Leu Cys Gln Ser Ile Leu His
1               5                  10                  15 att act cag ttg att ctg aga tgt tac tgt gct cct tgc agg agg tca      96
Ile Thr Gln Leu Ile Leu Arg Cys Tyr Cys Ala Pro Cys Arg Arg Ser
            20                  25                  30 ggc agt tct cca ggc tat ttg tac cga att gcc tac tcc ttg atc tgt     144
Gly Ser Ser Pro Gly Tyr Leu Tyr Arg Ile Ala Tyr Ser Leu Ile Cys
        35                  40                  45 gtt ctt ggc ctc ctg ggg aat att ctg gtg gtg atc acc ttt gct ttt     192
Val Leu Gly Leu Leu Gly Asn Ile Leu Val Val Ile Thr Phe Ala Phe
    50                  55                  60 tat aag aag gcc agg tct atg aca gac gtc tat ctc ttg aac atg gcc     240
Tyr Lys Lys Ala Arg Ser Met Thr Asp Val Tyr Leu Leu Asn Met Ala
65                  70                  75                  80 att gca gac atc ctc ttt gtt ctt act ctc cca ttc tgg gca gtg agt     288
Ile Ala Asp Ile Leu Phe Val Leu Thr Leu Pro Phe Trp Ala Val Ser
                85                  90                  95 cat gcc act ggt gcg tgg gtt ttc agc aat gcc acg tgc aag ttg cta     336
His Ala Thr Gly Ala Trp Val Phe Ser Asn Ala Thr Cys Lys Leu Leu
            100                 105                 110 aaa ggc atc tat gcc atc aac ttt aac tgc ggg atg ctg ctc ctg act     384
Lys Gly Ile Tyr Ala Ile Asn Phe Asn Cys Gly Met Leu Leu Leu Thr
        115                 120                 125 tgc att agc atg gac cgg tac atc gcc att gta cag gcg act aag tca     432
Cys Ile Ser Met Asp Arg Tyr Ile Ala Ile Val Gln Ala Thr Lys Ser
    130                 135                 140 ttc cgg ctc cga tcc aga aca cta ccg cgc agc aaa atc atc tgc ctt     480
Phe Arg Leu Arg Ser Arg Thr Leu Pro Arg Ser Lys Ile Ile Cys Leu
145                 150                 155                 160 gtt gtg tgg ggg ctg tca gtc atc atc tcc agc tca act ttt gtc ttc     528
Val Val Trp Gly Leu Ser Val Ile Ile Ser Ser Ser Thr Phe Val Phe
                165                 170                 175 aac caa aaa tac aac acc caa ggc agc gat gtc tgt gaa ccc aag tac     576
Asn Gln Lys Tyr Asn Thr Gln Gly Ser Asp Val Cys Glu Pro Lys Tyr
            180                 185                 190 can act gtc tcg gag ccc atc agg tgg aag ctg ctg atg ttg ggg ctt     624
Thr Thr Val Ser Glu Pro Ile Arg Trp Lys Leu Leu Met Leu Gly Leu
        195                 200                 205 gag cta ctc ttt ggt ttc ttt atc cct ttg atg ttc atg ata ttt tgt     672
Glu Leu Leu Phe Gly Phe Phe Ile Pro Leu Met Phe Met Ile Phe Cys
    210                 215                 220 tac acg ttc att gtc aaa acc ttg gtg caa gct cag aat tct aaa agg     720
Tyr Thr Phe Ile Val Lys Thr Leu Val Gln Ala Gln Asn Ser Lys Arg
225                 230                 235                 240 cac aaa gcc atc cgt gta atc ata gct gtg gtg ctt gtg ttt ctg gct     768
His Lys Ala Ile Arg Val Ile Ile Ala Val Val Leu Val Phe Leu Ala
                245                 250                 255 tgt cag att cct cat aac atg gtc ctg ctt gtg acg gct gct aat ttg     816
Cys Gln Ile Pro His Asn Met Val Leu Leu Val Thr Ala Ala Asn Leu
            260                 265                 270 ggt aaa atg aac cga tcc tgc cag agc gaa aag cta att ggc tat acg     864
Gly Lys Met Asn Arg Ser Cys Gln Ser Glu Lys Leu Ile Gly Tyr Thr
        275                 280                 285 aaa act gtc aca gaa gtc ctg gct ttc ctg cac tgc tgc ctg aac cct     912
Lys Thr Val Thr Glu Val Leu Ala Phe Leu His Cys Cys Leu Asn Pro
```

```
                    290                 295                 300
gtg ctc tac gct ttt att ggg cag aag ttc aga aac tac ttt ctg aag       960
Val Leu Tyr Ala Phe Ile Gly Gln Lys Phe Arg Asn Tyr Phe Leu Lys
305                 310                 315                 320 atc ttg aag gac ctg tgg tgt gtg aga agg aag tac aag tcc tca ggc      1008
Ile Leu Lys Asp Leu Trp Cys Val Arg Arg Lys Tyr Lys Ser Ser Gly
                325                 330                 335 ttc tcc tgt gcc ggg agg tac tca gaa aac att tct cgg cag acc agt     1056
Phe Ser Cys Ala Gly Arg Tyr Ser Glu Asn Ile Ser Arg Gln Thr Ser
                340                 345                 350 gag acc gca gat aac gac aat gcg tcg tcc ttc act atg tga             1098
Glu Thr Ala Asp Asn Asp Asn Ala Ser Ser Phe Thr Met
                355                 360                 365

<210> SEQ ID NO 8
<211> LENGTH: 365
<212> TYPE: PRT
<213> ORGANISM: Homo sapiens
<220> FEATURE:
<221> NAME/KEY: misc_feature
<222> LOCATION: (579)..(579)
<223> OTHER INFORMATION: unknown nucleotide

<400> SEQUENCE: 8

Met Phe Ser Thr Pro Val Lys Ile Ile Leu Cys Gln Ser Ile Leu His
1               5                   10                  15

Ile Thr Gln Leu Ile Leu Arg Cys Tyr Cys Ala Pro Cys Arg Arg Ser
                20                  25                  30

Gly Ser Ser Pro Gly Tyr Leu Tyr Arg Ile Ala Tyr Ser Leu Ile Cys
            35                  40                  45

Val Leu Gly Leu Leu Gly Asn Ile Leu Val Val Ile Thr Phe Ala Phe
    50                  55                  60

Tyr Lys Lys Ala Arg Ser Met Thr Asp Val Tyr Leu Leu Asn Met Ala
65                  70                  75                  80

Ile Ala Asp Ile Leu Phe Val Leu Thr Leu Pro Phe Trp Ala Val Ser
                85                  90                  95

His Ala Thr Gly Ala Trp Val Phe Ser Asn Ala Thr Cys Lys Leu Leu
            100                 105                 110

Lys Gly Ile Tyr Ala Ile Asn Phe Asn Cys Gly Met Leu Leu Leu Thr
        115                 120                 125

Cys Ile Ser Met Asp Arg Tyr Ile Ala Ile Val Gln Ala Thr Lys Ser
130                 135                 140

Phe Arg Leu Arg Ser Arg Thr Leu Pro Arg Ser Lys Ile Ile Cys Leu
145                 150                 155                 160

Val Val Trp Gly Leu Ser Val Ile Ile Ser Ser Ser Thr Phe Val Phe
                165                 170                 175

Asn Gln Lys Tyr Asn Thr Gln Gly Ser Asp Val Cys Glu Pro Lys Tyr
            180                 185                 190

Thr Thr Val Ser Glu Pro Ile Arg Trp Lys Leu Leu Met Leu Gly Leu
        195                 200                 205

Glu Leu Leu Phe Gly Phe Phe Ile Pro Leu Met Phe Met Ile Phe Cys
    210                 215                 220

Tyr Thr Phe Ile Val Lys Thr Leu Val Gln Ala Gln Asn Ser Lys Arg
225                 230                 235                 240

His Lys Ala Ile Arg Val Ile Ile Ala Val Val Leu Val Phe Leu Ala
                245                 250                 255

Cys Gln Ile Pro His Asn Met Val Leu Leu Val Thr Ala Ala Asn Leu
```

-continued

```
            260                 265                 270
Gly Lys Met Asn Arg Ser Cys Gln Ser Glu Lys Leu Ile Gly Tyr Thr
        275                 280                 285
Lys Thr Val Thr Glu Val Leu Ala Phe Leu His Cys Cys Leu Asn Pro
        290                 295                 300
Val Leu Tyr Ala Phe Ile Gly Gln Lys Phe Arg Asn Tyr Phe Leu Lys
305                 310                 315                 320
Ile Leu Lys Asp Leu Trp Cys Val Arg Arg Lys Tyr Lys Ser Ser Gly
                325                 330                 335
Phe Ser Cys Ala Gly Arg Tyr Ser Glu Asn Ile Ser Arg Gln Thr Ser
                340                 345                 350
Glu Thr Ala Asp Asn Asp Asn Ala Ser Ser Phe Thr Met
                355                 360                 365
```

METHOD FOR TREATING INFLAMMATORY CONDITIONS USING AN ANTIBODY TO MIP-3α

The present filing is a conversion to U.S. utility patent application from provisional U.S. Ser. No. 60/118,335, filed Feb. 3, 1999, which is incorporated herein by reference.

FIELD OF THE INVENTION

The invention relates generally to methods of using various chemokine related compositions, more particularly, to methods of treating skin diseases or conditions associated with misregulation of the chemokine MIP-3α, a ligand for the CCR6 chemokine receptor.

BACKGROUND

The immune system consists of a wide range of distinct cell types, each with important roles to play. See Paul (ed. 1997) *Fundamental Immunology* 4th ed., Raven Press, New York. The lymphocytes occupy central stage because they are the cells that determine the specificity of immunity, and it is their response that orchestrates the effector limbs of the immune system. Two broad classes of lymphocytes are recognized: the B lymphocytes, which are precursors of antibody secreting cells, and the T (thymus-dependent) lymphocytes. T lymphocytes express important regulatory functions, such as the ability to help or inhibit the development of specific types of immune response, including antibody production and increased microbicidal activity of macrophages. Other T lymphocytes are involved in direct effector functions, such as the lysis of virus infected-cells or certain neoplastic cells.

The chemokines are a large and diverse superfamily of proteins. The superfamily is subdivided into two classical branches, based upon whether the first two cysteines in the chemokine motif are adjacent (termed the "C-C" branch), or spaced by an intervening residue ("C-X-C"). A more recently identified branch of chemokines lacks two cysteines in the corresponding motif, and is represented by the chemokines known as lymphotactins. Another recently identified branch has three intervening residues between the two cysteines, e.g., CX3C chemokines. See, e.g., Schall and Bacon (1994) *Current Opinion in Immunology* 6:865–873; and Bacon and Schall (1996) *Int. Arch. Allergy & Immunol.* 109:97–109.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modulation of the effects of such factors. Thus, medical conditions where regulation of the development or physiology of relevant cells is required remain unmanageable.

SUMMARY OF THE INVENTION

The present invention is based, in part, upon the surprising discovery that the MIP-3α chemokine is expressed in inflamed skin cells. The chemokine is the ligand for the CCR6 receptor. See Greaves, et al. (1997) *J. Expt'l Med.* 186:837–844. Both the ligand and receptor are expressed at essentially undetectable levels in normal skin, while both are highly upregulated in inflamed skin.

The present invention provides methods of modulating migration of a cell within or to the skin of a mammal comprising administering to the mammal an effective amount of: an antagonist of MIP-3α; an agonist of MIP-3α, and antagonist of CCR6; or an agonist of CCR6. Typically, the migration is within the skin; or may be chemotactic or chemokinetic. In preferred embodiments, the administering is systemic, local, topical, subcutaneous, intracutaneous, or transdermal. Often, the cell is a T cell, B cell, dendritic cell, or dendritic cell precursor. In other embodiments, the cell is a T cell, or moves into the dermal and/or epidermal layers of the skin.

In other embodiments, the administering is of an antagonist of MIP-3α. Generally, the antagonist is selected from: a mutein of natural MIP-3α; an antibody which neutralizes MIP-3α; or an antibody which binds to CCR6. In various embodiments, the mammal is subject to a skin disease or condition, including one selected from cancer, cancer metastasis, skin transplant, or skin graft. Often, the antagonist is administered in combination with an antibiotic, antifungal, antiviral, or analgesic; or may be with an immune suppressive therapeutic, anti-inflammatory drug, growth factor, or immune adjuvant.

In another embodiment, the administering is with a primate MIP-3α. Often, the modulating is attracting the cell, e.g., to a site of cutaneous lesion. The primate MIP-30α may be administered in combination with an antibiotic, antifungal, antiviral, or analgesic; or with a vasodilator, growth factor, cytokine, anti-inflammatory drug, or immune adjuvant.

Alternatively, the invention provides a method of purifying a population of cells, the method comprising contacting the cells with MIP-3α, thereby resulting in the identification of cells expressing a receptor for MIP-3α. In certain embodiments, the receptor is CCR6, or the contacting results in specific migration of the cells to a site for purification, e.g., through pores of a membrane.

DETAILED DESCRIPTION OF THE INVENTION

Outline
I. General
II. Chemokine Agonists and Antagonists
   A. MIP-3α and Variants
   B. Antibodies
   C. Other Molecules
III. Immunoassays
IV. Uses
I. General The invention is based, in part, on the surprising discovery that the chemokine MIP-3α has been implicated in roles in skin immunity. In particular, MIP-3α has been identified as a ligand for the chemokine receptor designated CCR6. Both MIP-3α and CCR6 expression are undetectable in normal skin, while both are highly upregulated in inflamed skin samples.

The skin consists of a surface layer of epithelium called the epidermis and an underlying layer of connective tissue called the dermis. Under the dermis is a layer which contains large amounts of adipose tissue, the hypodermis. The skin serves a variety of functions, and variations in the character of the dermis and epidermis occur according to functional demands. The appendages of the skin, hair, nails, and sweat and sebaceous glands, are such local specializations of the epidermis. Together, the skin and its appendages form the integument. See, e.g., Fitzpatrick, et al. (eds. 1993) *Dermattology in General Medicine* 4th ed., McGraw-Hill, NY; Bos (ed. 1989) *Skin Immune System* CRC Press, Boca Raton, Fla.; Callen (1996) *General Practice Dermatology* Appleton and Lange; Rook, et al. (eds. 1998) *Textbook of Dermatology* Blackwell; Habifor and Habie (1995) *Clinical Dermatology: A Color Guide to Diagnosis and Therapy* Mosby; and Grob (ed. 1997) *Epidemiology, Causes and Prevention of Skin Diseases* Blackwell.

The epidermis consists of many different cell types in various proportions. The most prevalent cell type is keratinocytes, which make up some 95% of the cells. Cells in the 1–2% range include melanocytes and Langerhans cells. The Langerhans cells are particularly important because they trap antigens that have penetrated the skin, and transport antigens to regional lymph nodes. A small population of γδ T cells can also reside in the epidermis.

The dermis varies in thickness in different regions of the body. It is tough, flexible, and highly elastic, and consists of a feltwork of collagen fibers with abundant elastic fibers. The connective tissue is arranged into deep reticular and superficial papillary layers.

The chemokines are a sub-family of chemoattractant cytokines that were classically characterized by their ability to mediate leukocyte trafficking or migration by binding to specific G-protein-linked seven transmembrane spanning receptors, or GPCRs. Chemokines are divided into four groups based on the primary sequence of the first two cysteines: the CXC, CC, C, and CX3C families. The CXC and C families are effective predominantly on neutrophils and lymphocytes, respectively. The CC chemokines are preferentially effective on macrophages, lymphocytes, and eosinophils.

The chemokine MIP-3α, from human, mouse, and rat, has been described earlier. See, e.g., human, GenBank HSU77035; mouse, GenBank AF099052; rat, GenBank U90447; Li and Adams, WO 94-US9484; and Wilde, et al. WO 9616979; each of which is incorporated herein by reference for all purposes.

A primate, human, MIP-3α nucleic acid sequence is disclosed in SEQ ID NO: 1 and its corresponding amino acid sequence is disclosed in SEQ ID NO: 2. Of note, the CC motif is present at amino acid residues 6–7. A signal sequence is indicated, but based upon related genes; slightly different processing may occur in different cell types.

A murine, mouse, MIP-3α chemokine nucleic acid sequence is disclosed in SEQ ID NO: 3 and its corresponding amino acid sequence is disclosed in SEQ ID NO: 4. SignalP software predicts a cleavage between Ala(−1) and Ser1; but the actual cleavage may be on either side by a residue or so.

A murine, rat, MIP-3α chemokine nucleic acid sequence is disclosed in SEQ ID NO: 5 and its corresponding amino acid sequence is disclosed in SEQ ID NO: 6. SignalP software predicts a cleavage between Ala(−1) and Ala1; but the actual cleavage may be on either side by a residue or so.

In contrast to naive lymphocytes, memory/effector lymphocytes can access non-lymphoid effector sites and display restricted, often tissue-selective, migration behavior. This results in the presence of such lymphocytes in the peripheral tissues, e.g., outside of the lymphatic and blood volume.

Both human and mouse MIP-3α are detected in lymph nodes, appendix, PBL, fetal liver, fetal lung, and various cell lines. See, e.g., Rossi, et al. (1997) *J. Immunol.* 158:1033–1036; Hieshima, et al. (1997) *J. Biol. Chem.* 272:5846–5853; Baba, et al. (1997) *J. Biol. Chem.* 272:14893–14898; and Imai, et al. (1997) *J. Biol. Chem.* 272:15036–15042. The expression in the Langerhans islets suggests a role in skin functions. The data is consistent with MIP-3α as a product of activated monocytes, and is preferentially expressed in inflamed tissue. This distribution would suggest that MIP-3α may have a role in attracting memory T cells, and skin dendritic cells (Langerhans cells) and their precursors. These results suggest an important role for MIP-3α in recruitment of T cells and dendritic cells to peripheral cutaneous sites.

Chemokine receptors are members of the G protein coupled receptor family. See, e.g., Yoshie, et al. (1997) *J. Leukoc. Biol.* 62:634–644. CCR6 expression has been reported in Greaves, et al. (1997) *J. Expt'l Med.* 186:837–844; and Liao, et al., (1999) *J. Immunol.* 162:186–194. Northern blot data showed expression predominantly in the spleen, with lesser amounts in thymus, testis, small intestine, and peripheral blood. Additional transcripts were detected in spleen. Transcripts were not detected in the TF-1, Jurkat, MRC5, JY, and U937 cell lines. Message seems not to be abundantly expressed in the lymphoid lineage, particularly in, e.g., libraries made from cells made from dendritic cell cultures derived from cells selected on the basis of CD1a expression. Expression is lower in DC generated from monocytes.

Another study showed CCR6 was expressed on memory T cells, including most α4β7 memory cells and cutaneous lymphocyte-associated antigen expressing cells, and on B cells. Chemotaxis of T cells to MIP-3α was limited to memory cells. See Liao, et al. (1998) *J. Immunol.* 162:186–194. Antiserum detected CCR6 on CD34+ bone marrow derived dendritic cells.

Having identified the MIP-3α as a skin related chemokine, it will find use in affecting medical abnormalities of the skin. Common skin disorders involving the immune system include psoriasis, skin cancers, carcinomas, inflammation, allergies, dermatitis, wound healing, infections (both microbial and parasitic), and many others. See, e.g., *The Merck Manual*, particularly the chapter on dermatologic disorders. These therapeutics may have useful effects on growth or health of appendages of the skin, including, e.g., hair, nails, and sweat and sebaceous glands.

Psoriasis is a chronic inflammatory skin disease that is associated with hyperplastic epidermal keratinocytes and infiltrating mononuclear cells, including T cells, neutrophils and macrophages. Because of this highly mixed inflammatory picture and the resulting complex interrelationships between these different cells, it has been very difficult to dissect the mechanisms that underlie the induction and progression of the disease.

This view of psoriasis also implies that although dormant autoreactive T cells may pre-exist in susceptible individuals, an environmental stimulus is necessary to trigger disease induction. Others believe that the immune system plays only a minor modulatory role in the disease process and that hyperproliferation of keratinocytes is in fact the initiating event in a genetically susceptible host. Research into the pathogenesis of psoriasis has long been hindered by the lack of suitable animal models.

There is growing data indicating that T cells and not keratinocytes are the primary pathogenic component in the disease. The observations herein provide evidence to support the concept that psoriasis-like conditions can indeed result from unregulated T cell responses.

Skin cancers such as basal cell and squamous cell carcinoma are among the most common malignancies. See, e.g., Miller and Maloney (eds. 1997) *Cutaneous Oncology: Pathophysiology, Diagnosis, and Management* Blackwell; Emmett and Orourke (1991) *Malignant Skin Tumours* Churchill Livingstone; Friedman. (1990) *Cancer of the Skin* Saunders. Most of those tumors arise in sun exposed areas of the skin. Immune regulation or clearance of such tumors may depend upon function of the skin immune system. Cells which effect such may be compromised by local misregulation or suppression. The MIP-3α or antagonists may break a temporary homeostasis which suppresses normal immune response, thereby leading to activation of proper regulatory and immune pathways.

Dermatitis is a superficial inflammation of the skin, characterized by vesicles (when acute), redness, edema, oozing, crusting, scaling, and/or itching. See, e.g., Lepoittevin (ed. 1998) *Allergic Contact Dermatitis: The Molecular Basis* Springer-Verlag; Rietschel and Fowler (eds. 1995) *Fisher's Contact Dermatitis* Lippincott; and Rycroft, et al. (eds. 1994) *Textbook of Contact Dermatitis* Springer-Verlag. The term eczematous dermatitis is often used to refer to a vesicular dermatitis. Dermatitis may accompany various immune deficiency conditions or diseases, inborn metabolic disorders, or nutritional deficiency diseases. Certain of the symptoms of such conditions may be treated using the present invention.

Pruritus is a sensation that the patient attempts to relieve by scratching. See, e.g., Fleischer and Fleischer (1998) *The Clinical Management of Itching: Therapeutic Protocols for Pruritus* Parthenon. Many parasitic or infectious conditions may result in those symptoms, which conditions may be cleared by proper reactivation or suppression of immune functions in the skin. Likewise with various allergic or other immune reactions to exposure to various allergic or inflammatory antigens.

II. Chemokine Agonists and Antagonists

Mammalian MIP-3α chemokines were described previously in WO 98/01557, which describes various migratory assays. Various agonists and antagonists of the natural ligands can be produced. The migration assays may take advantage of the movement of cells through pores in membranes. Chemotaxis may be measured thereby. Alternatively, chemokinetic assays may be developed, which measure the induction of kinetic movement, not necessarily relative to a gradient, per se.

A. MIP-3α and Variants

MIP-3α agonists will exhibit some or all of the signaling functions of MIP-3α, e.g., binding, inducing a Ca++ flux, and chemoattracting appropriate receptor bearing cells. Various mammalian MIP-3α sequences may be evaluated to determine what residues are conserved across species, suggesting what residues may be changed without dramatic effects on biological activity. Alternatively, conservative substitutions are likely to retain biological activity, thus leading to variant forms of the chemokine which will retain agonist activity. Standard methods for screening mutant or variant MIP-3α polypeptides will determine what sequences will be useful therapeutic agonists.

In addition, certain nucleic acid expression methods may be applied. For example, in skin graft contexts, it may be useful to transfect the grafts with nucleic acids which will be expressed, as appropriate. Various promoters may be operably linked to the gene, thereby allowing for regulated expression. Antisense constructs may prevent expression of the ligand or receptor.

Alternatively, antagonist activity may be tested or screened for. Tests for ability to antagonize chemoattractant activity can be developed using assays as described below. Various ligand homologs can be created which retain receptor binding capacity, but lack signaling capability, thus serving as competitive binding molecules. Small molecules may also be screened for ability to antagonize MIP-3α function, e.g., chemoattraction, receptor binding, Ca++ flux, and other effects mediated by MIP-3α. See generally Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa., each of which is incorporated herein by reference.

B. Antibodies

The present invention provides for the use of an antibody or binding composition which specifically binds to MIP-3α, preferably mammalian, e.g., primate, human, cat, dog, rat, or mouse, and neutralizes the ability of the chemokine to mediate its signal. Antibodies can be raised to various MIP-3α proteins, including individual, polymorphic, allelic, strain, or species variants, and fragments thereof, either in their naturally occurring (full-length) forms or in their recombinant forms. Additionally, antibodies can be raised to MIP-3α or polypeptides in both their native (or active) forms or in their inactive, e.g., denatured, forms, which may neutralize ligand capacity to mediate its signal. Antibodies may block the interaction of the ligand with its receptor.

Alternatively, receptor antagonists may be produced by making antibodies which bind to the receptor and block ligand binding. With the identification of the CCR6 as a receptor for the cytokine, antibodies to the receptor may be selected for those which block the binding of, or signaling induced by, ligand.

A number of immunogens may be selected to produce antibodies specifically reactive, or selective for binding, with MIP-3α or CCR6 proteins. Recombinant protein is a preferred immunogen for the production of monoclonal or polyclonal antibodies. Naturally occurring protein, from appropriate sources, e.g., primate, rodent, etc., may also be used either in pure or impure form. Synthetic peptides, made using the MIP-3α or CCR6 protein sequences described herein, may also be used as an immunogen for the production of antibodies. Recombinant protein can be expressed and purified in eukaryotic or prokaryotic cells as described, e.g., in Coligan, et al. (eds. 1995 and periodic supplements) *Current Protocols in Protein Science* John Wiley & Sons, New York, N.Y.; and Ausubel, et al (eds. 1987 and periodic supplements) *Current Protocols in Molecular Biology*, Greene/Wiley, New York, N.Y. Naturally folded or denatured material, perhaps expressed on cell surfaces, can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to, e.g., the MIP-3α, protein or polypeptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane *Antibodies, A Laboratory Manual*; or Coligan (ed.) *Current Protocols in Immunology*. Immunization can also be performed through other methods, e.g., DNA vector immunization. See, e.g., Wang, et al. (1997) *Virology* 228:278–284. Affinity purification, or absorptions, can be used to select for desired specificity of binding.

Monoclonal antibodies may be obtained by various techniques familiar to those skilled in the art. Typically, spleen cells from an animal immunized with a desired antigen are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies or binding compositions, including binding fragments and single chain versions, against predetermined fragments of MIP-3α or CCR6 polypeptides can be raised by immunization of animals with conjugates of the fragments with carrier proteins as described above. Monoclonal antibodies are prepared from cells secreting the desired antibody. These antibodies can be screened for binding to normal or defective MIP-3α protein, or screened for capacity to block cell MIP-3α mediated chemoattraction or chemokinetic activity. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156.

Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

C. Other Molecules

Antibodies are merely one form of specific binding compositions. Other binding compositions, which will often have similar uses, include molecules that bind with specificity to MIP-3α receptor, e.g., CCR6, in a binding partner-binding partner fashion, an antibody-antigen interaction, or in a natural physiologically relevant protein-protein interaction, either covalent or non-covalent, e.g., proteins which specifically associate with MIP-3α receptor protein. The molecule may be a polymer, or chemical reagent. A functional analog may be a protein with structural modifications, or may be a structurally unrelated molecule, e.g., which has a molecular shape which interacts with the appropriate binding determinants. Application of, e.g., Systematic Evolution of Ligand by Exponential Enrichment (SELEX) technology, methods are available to select specific binding constructs for desired targets. See, e.g., Colas, et al. (1996) *Nature* 380:548–550; Cohen, et al. (1998) *Proc. Nat'l Acad. Sci. USA* 95:14272–14277; Kolonin, et al. (1998) *Proc. Nat'l Acad. Sci. USA* 95:14266–14271; Famulok, et al. (1998) *Curr. Opin. Chem. Biol.* 2:320–327; and Eaton, et al. (1997) *Bioorg. Med. Chem.* 5:1087–1096.

Drug screening using antibodies or MIP-3α or fragments thereof can be performed to identify compounds having binding affinity to MIP-3α, or can block or simulate the natural interaction with ligand. Subsequent biological assays can then be utilized to determine if the compound has intrinsic blocking activity and is therefore an antagonist. Likewise, a compound having intrinsic stimulating activity can signal to the cells via the MIP-3α pathway and is thus an agonist in that it simulates the activity of a ligand. Mutein antagonists may be developed which maintain receptor binding but lack signaling.

Structural studies of the ligands will lead to design of new variants, particularly analogs exhibiting agonist or antagonist properties on the receptor. This can be combined with previously described screening methods to isolate muteins exhibiting desired spectra of activities.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. See, e.g., meetings on High Throughput Screening, International Business Communications, Southborough, Mass. 01772-1749. Such molecules may compete with natural ligands, and selectively bind to the MIP-3α or CCR6

III. Immunoassays

Immunoassays are valuable in diagnosing a disease or disorder associated with MIP-3α imbalance or pathology. Qualitative or quantitative measurement of a particular protein can be performed by a variety of immunoassay methods. For a review of immunological and immunoassay procedures in general, see Stites and Terr (eds. 1991) *Basic and Clinical Immunology* (7th ed.). Moreover, the immunoassays of the present invention can be performed in many configurations, which are reviewed extensively in, e.g., Maggio (ed. 1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane *Antibodies: A Laboratory Manual*, supra; Chan (ed. 1987) *Immunoassay: A Practical Guide* Academic Press, Orlando, Fla.; Price and Newman (eds. 1991) *Principles and Practice of Immunoassays* Stockton Press, NY; and Ngo (ed. 1988) *Non-isotopic Immunoassays* Plenum Press, NY.

In particular, the present invention provides various skin related diseases as conditions susceptible to analysis or diagnosis by evaluating MIP-3α and/or CCR6. For example, the likelihood of skin rejection in a graft situation would be evaluated by the numbers or types of MIP-3α or CCR6 bearing cells present. Prophylactic downregulation may be useful to prevent the recruitment of dermal T or NK cells. Response to various skin tumors may be evaluated by the presence or absence of MIP-3α and/or CCR6 bearing cells.

Immunoassays for measurement of MIP-3α proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with MIP-3α proteins produced as described above. The concentration of labeled analyte bound to the capture agent is inversely proportional to the amount of free analyte present in the sample.

In a competitive binding immunoassay, typically the MIP-3α protein present in the sample competes with labeled protein for binding to a specific binding agent, e.g., an antibody specifically reactive with the MIP-3α protein. The binding agent may be bound to a solid substrate or surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

MIP-3α proteins may also be determined by a variety of noncompetitive immunoassay methods. For example, a two-site, solid phase sandwich immunoassay may be used. In this type of assay, a binding agent for the protein, e.g., an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of MIP-3α or CCR6 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $^3$H, $^{125}$I, 35S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904.

Antibodies reactive with a particular protein can also be measured by a variety of immunoassay methods. Thus modifications of the above procedures may be used to determine the amounts or affinities of various MIP-3α or CCR6 antibodies or antibody preparations. For a review of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

Screens to evaluate the binding and activity of mAbs and binding compositions encompass a variety of methods. Binding can be assayed by detectably labeling the antibody or binding composition as described above. Cells responsive to MIP-3α can be used to assay antibody or binding composition.

To evaluate MIP-3α chemoattraction or chemokinetic ability, experimental animals, e.g., mice, are preferably used. Skin, e.g., Langerhans, cell counts are made prior to and at various time points after administration of a bolus of the candidate agonist or antagonist. Levels are analyzed in various samples, e.g., blood, serum, nasal or pulmonary lavages, or tissue biopsy staining. A successful depleting mAb or binding composition will significantly lower the level of CCR6 bearing cells. Such may be at least about 10%, preferably at least about 20%, 30%, 50%, 70%, or more.

Evaluation of antibodies can be performed in other animals, e.g., humans using various methods. For example, blood samples are withdrawn from patients suffering from a skin related disease or disorder before and after treatment with a candidate mAb.

IV. Uses

The exquisite tissue-selective homing of lymphocytes has long been appreciated as central for the control of systemic immune responses. Recent advances in the field support a model in which leukocyte homing is achieved by sequential engagement of differentially expressed and independently regulated vascular and leukocyte adhesion molecules, and signaling receptors and their ligands. Butcher and Picker (1996) *Science* 272:60–66. The observation that chemokines, a superfamily of small secreted proteins with G protein-coupled receptors (Baggiolini (1998) *Nature* 392:565–568) can attract leukocytes led to the hypothesis that chemokines provide key signals directing recruitment of T lymphocyte subsets into lymphoid and extra-lymphoid immune effector sites. The inflamed skin-specific expression of MIP-3α and CCR6 suggests that such skin-specific chemokines selectively attract functional subsets of lymphocytes into the skin.

As such, the present invention provides means to purify desired skin cell subsets. The chemoattractive or chemokinetic effects on those cells can be the basis of purification methods. Methods exist for selective migration and recovery of cells to or from the chemokine, e.g., through porous membrane, or to various locations in a culture. Other methods exist to selectively separate cells of particular shapes from others. Alternatively, labeling can be used to FACS sort cells which specifically bind the chemokine. Populations of substantially homogeneous Langerhans or skin derived cells will have important utility in research or therapeutic environments.

While MIP-3α is likely to have functional effects on CCR6 bearing subsets of cells, e.g., T and B cells and precursors, other cells which may also be responsive include dendritic cells or granulocytes, e.g., neutrophils and/or eosinophils, or their precursors. Effects on various cell types may be indirect, as well as direct. A statistically significant change in the numbers of cells will typically be at least about 10%, preferably 20%, 30%, 50%, 70%, 90%, or more. Effects of greater than 100%, e.g., 130%, 150%, 2X, 3X, 5X, etc., will often be desired. The effects may be specific in causing chemotaxis to specific points, or may be chemokinetic, in inducing general movement of cells, but not necessarily in a specific direction, e.g., of concentration gradient.

The present invention will be useful in the treatment of medical conditions or diseases associated with immunological conditions of the skin. See, e.g., Bos (ed. 1990) *Skin Immune System* CRC Press, Boca Raton, Fla.; Fitzpatrick, et al. (eds. 1993) *Dermatology in General Medicine* (4th ed.) McGraw-Hill, NY.; Rook, et al. (eds. 1998) *Textbook of Dermatology* Blackwell; Habifor and Habie (1995) *Clinical Dermatology: A Color Guide to Diagnosis and Therapy* Mosby; Grob (ed. 1997) *Epidemiology, Causes and Prevention of Skin Diseases* Blackwell; Frank, et al. (eds. 1995) *Samter's Immunologic Diseases,* 5th Ed., vols. I–II, Little, Brown and Co., Boston, Mass.; Coffman, et al (1989) *Science* 245:308–310; and Frick, et al. (1988) *J. Allergy Clin. Immunol.* 82:199–225. The agonists or antagonists described may be combined with other treatments of the medical conditions described herein, e.g., an antibiotic, antifungal, antiviral, immune suppressive therapeutic, immune adjuvant, analgesic, anti-inflammatory drug, growth factor, cytokine, vasodilator, or vasoconstrictor. See, e.g, the Physician's Desk Reference, both prescription and non-prescription compendiums.

The CCR6 receptor appears to be preferentially expressed on CD4+ memory T cells. Its ligand, MIP-3α, is an inflammatory chemokine expressed by cellular constituents of the skin, whose expression is inducible after stimulation with T cell-derived proinflammatory meidators such as IFN-γ and IL-17. Thus, CD4+ memory T cell mediated skin conditions are therapeutic targets of the antagonists, e.g., psoriasis, atopic dermatitis, contact dermatitis, SLE, and lichen ruber planus.

Preferred combination therapies include the MIP-3α reagent with various anti-inflammatory agents, such as topical, transdermal, or systemic steroids or corticosteroids. Systemic, topical, transdermal, or systemic retinoid or retinoid-like compounds, or vitamin D analogs, may be administered with the MIP-3α therapeutics. Alternatively, various forms of UV light may be used in combination with these therapeutics, e.g., ultraviolet A, ultraviolet B, or narrow bands of UVB.

For example, the MIP-3α ligands would be expected to signal specifically to the cell types expressing their receptor. Thus, it will be possible to block signaling, e.g., to the T cell or B cell subsets, by reagents which block receptor signaling, e.g., antibodies to ligand, and small drug antagonists.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes 70, 73, 74, 84, 92, 93, 108, 116, 121, 132, 150, 162, and 163. These will allow use of the reagents for purifying cell subpopulations, etc.

To prepare pharmaceutical or sterile compositions including, e.g., MIP-3α, the material is admixed with a pharmaceutically acceptable carrier or excipient which is preferably inert. Preparation of such pharmaceutical compositions is known in the art, see, e.g., *Remington's Pharmaceutical Sciences* and *U.S. Pharmacopeia: National Formulary,* Mack Publishing Company, Easton, Pa. (1984). Typically, therapeutic compositions are sterile. Alternatively, MIP-3α antagonist compositions can be prepared.

Agonists, e.g., natural ligand, or antagonists, e.g., antibodies or binding compositions, are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863. However, as a skin target, the administration may be topical, transdermal, intradermal, subcutaneous, or even systemic.

When administered parenterally the therapeutics will be formulated in a unit dosage injectable form (solution, suspension, emulsion) in association with a pharmaceutically acceptable parenteral vehicle. Such vehicles are inherently nontoxic and nontherapeutic. The antagonist may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ), intradermal (ID), or intramuscular (IM) injection. The proportion of therapeutic entity and additive can be varied over a broad range so long as both are present in effective amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; Lieberman, et al. (eds. 1990) *Pharmaceutical Dosage Forms: Disperse Systems* Dekker, NY; Fodor, et al. (1991) *Science* 251:767–773; Coligan (ed.) *Current Protocols in Immunology;* Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography*, Academic Press, New York. Local, e.g., topical or transdermal, administration will often be particularly useful.

Selecting an administration regimen for a therapeutic agonist or antagonist depends on several factors, including the serum or tissue turnover rate of the therapeutic, the immunogenicity of the therapeutic, or the accessibility of the target cells. Preferably, an administration regimen maximizes the amount of therapeutic delivered to the patient consistent with an acceptable level of side effects. Accordingly, the amount of therapeutic delivered depends in part on the particular agonist or antagonist and the severity of the condition being treated. Guidance in selecting appropriate doses of antibodies is found in the literature on therapeutic uses, e.g. Bach et al., chapter 22, in Ferrone, et al. (eds. 1985) *Handbook of Monoclonal Antibodies* Noges Publications, Park Ridge, N.J.; and Russell, pgs. 303–357, and Smith et al., pgs. 365–389, in Haber, et al. (eds. 1977) *Antibodies in Human Diagnosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Numbers of CCR6 bearing cells in defined samples might be important indicators of when an effective dose is reached. Preferably, an antibody or binding composition thereof that will be used is derived from the same species as the animal targeted for treatment, thereby minimizing a humoral response to the reagent.

The total weekly dose ranges for antibodies or fragments thereof, which specifically bind to MIP-3α, range generally from about 1 ng, more generally from about 10 ng, typically from about 100 ng; more typically from about 1 μg, more typically from about 10 μg, preferably from about 100 μg, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 μg, preferably at least about 50 μg, and more preferably at least about 100 μg per kilogram of body weight. Generally, the range will be less than about 1000μg, preferably less than about 500 μg, and more preferably less than about 100 μg per kilogram of body weight. Dosages are on a schedule which effects the desired treatment and can be periodic over shorter or longer term. In general, ranges will be from at least about 10 μg to about 50 mg, preferably about 100 μg to about 10 mg per kilogram body weight.

Other antagonists of the ligands, e.g., muteins, are also contemplated. Hourly dose ranges for muteins range from at least about 10 μg, generally at least about 50 μg, typically at least about 100 μg, and preferably at least 500 μg per hour. Generally the dosage will be less than about 100 mg, typically less than about 30 mg, preferably less than about 10 mg, and more preferably less than about 6 mg per hour. General ranges will be from at least about 1μg to about 1000 μg, preferably about 10 μg to about 500 μg per hour.

In particular contexts, e.g., transplant or skin grafts, may involve the administration of the therapeutics in different forms. For example, in a skin graft, the tissue may be immersed in a sterile medium containing the therapeutic resulting in a prophylactic effect on cell migration soon after the graft is applied.

The present invention also provides for administration of MIP-3α antibodies or binding compositions in combination with known therapies, e.g., steroids, particularly glucocorticoids, which alleviate the symptoms associated with excessive inflammatory responses. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day.

The phrase "effective amount" means an amount sufficient to effect a desired response, or to ameliorate a symptom or sign of the skin condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Alternatively, modulation of migration will mean that the migration or trafficking of various cell types is affected. Such will result in, e.g., statistically significant and quantifiable changes in the numbers of cells being affected. This may be an increase or decrease in the numbers of target cells being attracted within a time period or target area.

The present invention provides reagents which will find use in therapeutic applications as described elsewhere herein, e.g., in the general description for treating disorders associated with skin conditions. See, e.g., Berkow (ed.) *The Merck Manual of Diagnosis and Therapy*, Merck & Co., Rahway, N.J.; Thorn, et al. *Harrison's Principles of Internal Medicine*, McGraw-Hill, NY; Gilman, et al. (eds. 1990) *Goodman and Gilman's: The Pharmacological Bases of Therapeutics,* 8th Ed., Pergamon Press; *Remington's Pharmaceutical Sciences,* 17th ed. (1990), Mack Publishing Co., Easton, Pa.; Langer (1990) *Science* 249:1527–1533; and *Merck Index*, Merck & Co., Rahway, N.J.

Antibodies to MIP-3α proteins may be used for the identification or sorting of cell populations expressing MIP- 3α protein, e.g., fibroblasts or Langerhans cells. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells expressing the MIP-3α receptor, e.g., CCR6,; can also be purified, e.g., using magnetic beads as described, e.g., in Bieva, et al. (1989) *Exp. Hematol.* 17:914–920; Hernebtub, et al. (1990) *Bioconj. Chem.* 1:411–418; Vaccaro (1990) *Am. Biotechnol. Lab.* 3:30.

Moreover, antisense nucleic acids may be used. For example, antisense polynucleotides against the ligand encoding nucleic acids may function in a manner like ligand antagonists, and antisense against the receptor may function like receptor antagonists. Thus, it may be possible to block the signaling through the pathway with antisense nucleic acids. Conversely, nucleic acids for the receptor may serve as agonists, increasing the numbers of receptor on the cell, thereby increasing cell sensitivity to ligand, and perhaps blocking the normal apoptotic signal described.

Using the assay methods described above, the antibodies or binding compositions are useful in diagnosing diseases states which result in skin disorders. Antibodies raised against a MIP-3α or CCR6 protein will also be useful to raise anti-idiotypic antibodies. These will be useful in detecting or diagnosing various immunological conditions related to expression of the respective antigens. Combinations of these signals may be also pursued.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science*, John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163.

Lymphocyte migration assays are performed as previously described, e.g., in Bacon, et al. (1988) *Br. J. Pharmacol.* 95:966–974. Other trafficking assays are also available. See, e.g., Quidling-Järbrink, et al. (1995) *Eur. J. Immunol.* 25:322–327; Koch, et al. (1994) *J. Clinical Investigation* 93:921–928; and Antony, et al. (1993) *J. Immunol.* 151:7216–7223.

Alternatively, an activation assay or attraction assay is used. An appropriate cell type is selected, e.g., hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Chemokines may also be assayed for activity in hemopoietic assays as described, e.g., by H. Broxmeyer. See Bellido, et al. (1995) *J. Clinical Investigation* 95:2886–2895; and Jilka, et al. (1995) *Expt'l Hematology* 23:500–506. They may be assayed for angiogenic activities as described, e.g., by Streiter, et al. (1992) *Am. J. Pathol.* 141:1279–1284. Or for a role in inflammation. See, e.g., Wakefield, et al. (1996) *J. Surgical Res.* 64:26–31.

Other assays will include those which have been demonstrated with other chemokines. See, e.g., Schall and Bacon (1994) *Current Opinion in Immunology* 6:865–873; and Bacon and Schall (1996) *Int. Arch. Allergy & Immunol.* 109:97–109. Ca2+ flux upon chemokine stimulation is measured according to the published procedure described in Bacon, et al. (1995) *J. Immunol.* 154:3654–3666.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cell Culture and Tissue Samples

Adult human primary cells including keratinocytes, melanocytes, and dermal fibroblasts are obtained from Clonetics and cultured according to the suppliers instructions. For cytokine treatment, cells are cultured with 10 ng/ml hTNF-α plus 3 ng/ml hIL-1β (R&D Systems) in culture medium. Human T cells are purified from PBMCs using a T-cell enrichment column (R&D Systems) according to the manufacturers instructions.

III. Isolation of Encoding Sequences

The human, mouse, or rat MIP-3α sequence is readily available. The nucleic acid and amino acid sequences for human, mouse and rat MIP-3α are disclosed in SEQ ID NOs: 1–2, SEQ ID NOs: 3–4, and SEQ ID NOs: 5–6, respectively. See also GenBank. Appropriate PCR primes or hybridization probes can be selected.

Similarly, the human CCR6, or others, can be readily isolated. The nucleic acid and amino acid sequences for human CCR6 are disclosed in SEQ ID NOs: 7–8. See also GenBank.

IV. Distribution Analysis

For Southern blotting, 5 μg of each cDNA library is digested with the appropriate restriction enzymes to release the insert, subjected to gel electrophoresis, and transferred to Hybond-N+ membrane. For Northern blotting all RNAs are isolated using RNAzol B (TEL-TEST, Inc.) and analyzed by electrophoresis on a 1% formaldehyde-agarose gel and transferred to Hybond-N+ membrane. Northern and Southern blots are hybridized for 16 hr at 65° C. with $^{32}$P-labeled probes obtained by randomly priming (Prime-it; Stratagene) the full length inserts from mouse or human MIP-3α or CCR6 clones. After hybridization, blots are washed at high stringency and exposed to film.

The MIP-3α was identified from a cDNA library made from human monocytes activated with LPS and IFN-γ, in the presence of anti-IL-10. See, Rossi, et al. (1997) *J. Immunology* 158:1033–1036. Message of the chemokine has also been detected in pancreatic islet cells, fetal lung, and hepatic HEPG2 cells, suggesting a physiological role in inflammation or medical conditions in such organs/tissues.

The gene is expressed in HL-60 (promyelocytic leukemia); S3 (HeLa cell); K562 (chronic myelogenous leukemia); MOLT-4 (lymphblastic leukemia); Raji (Burkitt's lymphoma); SW480 (colorectal adenocarcinoma); A549 (lung carcinoma); and G361 (melanoma) cell lines, as determined by probing on a tissue blot from CLONTECH. Tissue expression gave a positive signal in lymph node, appendix, peripheral blood lymphocytes, fetal liver, and fetal lung, suggesting a physiological role in inflammation or medical conditions in such organs/tissues; but no detectable signal in spleen, bone marrow, brain, and kidney.

The main transcript appears to be about 1.2 kb, with two additional transcript sizes in fetal lung RNA. Among the various tissues, transcript sizes of 1.8, 2.7, and 4.2 kb were detected.

Positive signals were also detected in the following cDNA libraries: dendritic cells activated with LPS, but not when activated with GM-CSF and IL-4; monocytes treated with LPS, IFN-γ, and anti-IL-10, but not when treated with LPS, IFN-γ, and IL-10; and activated PBMC.

These expression data implicate this chemokine in inflammatory responses upon cell activation. The lymph nodes, appendix, and PBL are sites where inflammatory processes take place. The MIP-3α may exert its effects on monocytes and cells involved in inflammatory events. Other structural features implicate this chemokine in eosinophil and lung physiology, e.g., asthma indications. Thus, an antagonist of the chemokine, e.g., an antibody, may be important for treatment of asthmatic conditions. Also, IL-10 appears to inhibit MIP-3α expression.

The human MIP-3α is a ligand for the CCR6. Thus, a positive control exists for the Ca++ flux assay for that receptor. This allows for the further screening of agonist ligands for the CCR6. Moreover, the CCR6 was isolated from eosinophil cDNA, and observations have been made that eosinophils migrate to MIP-3α in vitro. See, e.g., Greaves, et al. (1997) *J. Exp. Med.* 186:837–844; Liao, et al. (1997) *Biochem. Biophys. Res. Commun.* 236:212–217; and Liao, et al. (1998) *J. Immunol.* 162:186–194. These suggest that the MIP-3α interaction with the CCR6 is important in recruitment of eosinophils, as occurs with the eotaxin ligand and the CCR3. As such, antagonists of the MIP-3α interaction with the CCR6 will likely be useful in inhibiting eosinophilia, particularly in the lung, or lung inflammation. These may accompany asthmatic or other pulmonary conditions. The specific upregulation of the pair in inflamed skin suggests a role in skin immunity.

The CCR6 was isolated from a cDNA library made from a dendritic cell cDNA library. It appears to be expressed in certain T cells, spleen cell subsets, NK cells, and other cell populations enriched in dendritic cells, including CD1a+, CD14+, and CD1Aa+ cells. It did not give a detectable signal in TF1, Jurkat, MRC5, JY, or U937 cell lines.

Quantitative PCR methods have been applied, e.g., TAQ-MAN™. High levels of CCR6 cDNA was detected in libraries made from peripheral blood mononuclear cells, resting; T cell, TH0 clone Mot 72, resting; T cell, TH1 clone HY06, anergic; T cell clones, pooled, resting; T cell γδ clones, resting; Splenocytes, resting; Splenocytes, activated; B cell EBV lines, resting; NK 20 clones pooled, resting; NK cell clone, NKA6; NK cytotoxic clone, resting; NK cell clone, NK non cytotox; monocytes, LPS, γIFN, anti-IL-10, 4+16 hr; monocytes, LPS, γIFN, IL10, 4+16 hr; DC 70% CD1a+, ex CD34+ GM-CSF, TNFα, activated 1 hr; DC 70% CD1a+, ex CD34+ GM-CSF, TNFα, activated 6 hr; DC 95% CD1a+, ex CD34+ GM-CSF, TNFα, activated 1+6 hr; DC 95% CD14+, ex CD34+ GM-CSF, TNFα, activated 1+6 hr; DC CD1a+ CD86+, ex CD34+ GM-CSF, TNFα, activated 1+6 hr; DC resting CD34 derived; DC CD4lo activated mo derived; DC resting activated mo derived; DC TGF and TGFb CD34 derived; lung fetal; gall bladder fetal; small intestine fetal; ovary fetal; spleen fetal; normal human colon; normal human thyroid; tonsil inflammed; pool of three heavy smoker human lung samples; allergic lung sample; Hashimoto's thyroiditis thyroid sample; and Psoriasis patient skin sample. Intermediate levels were detected in libraries derived from peripheral blood mononuclear cells, activated; T cell, TH0 clone Mot 72, activated; T cell, TH0 clone Mot 81, resting; T cell, TH0 clone Mot 81, Activated; T cell, TH1 clone HY06, resting; T cell, TH1 clone HY06, activated; B cell line JY, activated; NK 20 clones pooled, activated; NK cell clone, NKB1, pSPORT; NK cell clone, NKB1; DC ex monocytes GM-CSF, IL-4, resting; DC ex monocytes GM-CSF, IL-4, monokine activated 4+16 hr; eosinophils; testes fetal; placenta 28 wk; pool of two normal human lung samples; ulcerative colitis human colon sample; pool of rheumatoid arthritis samples, human; and normal w.t. monkey colon. Low or undetectable levels were detected in libraries from T cell, TH0 clone Mot 72, anergic; T cell, TH2 clone HY935, resting; T cell, TH2 clone HY935, activated; T cell, TH1 clone TA20-23, resting; T cell, TH1 clone TA20-23, activated; T cell, TH0 clone B21, resting; T cell, TH0 clone B21, Activated; T cells CD4+, TH2 polarized, activated; T cell lines Jurkat and Hut78, resting; U937 premonocytic line, resting; U937 premonocytic line, activated; monocytes, LPS, γIFN, anti-IL-10; monocytes, LPS, γIFN, IL-10; monocytes, LPS, 1 hr; monocytes, LPS, 6 hr;, DC 70% CD1a+, ex CD34+ GM-CSF, TNFα, resting; DC ex monocytes GM-CSF, IL-4, resting; DC ex monocytes GM-CSF, IL-4, LPS activated 4+16 hr; kidney fetal; liver fetal; heart fetal; brain fetal; Allergic lung #19; adipose tissue fetal; uterus fetal; normal human skin; *Pneumocystic carnii* pneumonia lung sample; normal w.t. monkey lung; Ascaris-challenged monkey lung, 24 hr.; and Ascaris-challenged monkey lung, 4 hr.

Being found on dendritic cells, its ligand, including the MIP-3α, may be important in attracting appropriate cells for the initiation of an immune response. MIP-3α has been shown to be a very potent chemoattractant for dendritic cells. Significant roles of the ligand and receptor in skin physiology are suggested. The receptor may be also present in other cells important in such responses.

V. Chemotaxis

Recombinant mouse MIP-3α0 is produced in *E. coli* and purified, e.g., as previously described for other. chemokines. Hedrick, et al. (1998) *Blood* 91:4242–4247. Total human T cells in DMEM, pH 6.9, 1% bovine serum albumin, were added to the top chamber of 3 μm pore polycarbonate Transwell culture insert (Costar) and incubated with the indicated concentrations of purified chemokine in the bottom chamber for 3 h. The number of migrating cells of each subtype is determined by multi-parameter flow cytometry using fluorochrome conjugated antibodies. A known number of 15 µm microsphere beads (Bangs Laboratories, Fishers, Ind.) is added to each sample before analysis in order to determine the absolute number of migrating cells.

Chemotaxis assays are performed with purified human peripheral-blood T cells and/or skin-homing T cells. Other cell types express the CCR6, e.g., T cells, B cells, DC cells, and granulocyte cells, e.g., neutrophils and/or eosinophils. Recombinant murine MIP-3α should have effects on the cell types expressing CCR6.

The MIP-3α and CCR6 expression levels are very low in normal skin samples, but are highly upregulated in inflamed skin tissues.

VI. Antibody Production

Appropriate mammals are immunized with appropriate amounts, e.g., of MIP-3α or MIP-3α gene transfected cells, e.g., intraperitoneally every 2 weeks for 8 weeks. Similar methods may be used to produce antibodies which bind to CCR6, e.g., purified CCR6, polypeptides, or transfected cells expressing the receptor may be used. Typically, rodents are used, though other species should accommodate production of selective and specific antibodies. The final immunization is given intravenously (IV) through the tail vein.

Generic polyclonal antibodies may be collected. Alternatively, monoclonal antibodies can be produced. For example, four days after the IV injection, the spleen is removed and fused to SP2/0 and NS1 cells. HAT resistant hybridomas are selected, e.g., using a protocol designed by Stem Cell Technologies (Vancouver, BC). After 10 days of HAT selection, resistant foci are transferred to 96 well plates and expanded for 3 days. Antibody containing supernatants are analyzed, e.g., by FACS for binding to NIH3T3/surface MIP-3α transfectants. Many different MIP-3α mAbs are typically produced. Those antibodies may be isolated and modified, e.g., by labeling or other means as is standard in the art. See, e.g., Harlow and Lane (1988) *Antibodies: A Laboratory Manual* CSH Press; Goding (1986) *Monoclonal Antibodies: Principles and Practice* (2d ed.) Academic Press, New York, N.Y. Methods to conjugate magnetic reagents, toxic entities, labels, attach the antibodies to solid substrates, to sterile filter, etc., are known in the art.

VII. Purification of Cells

MIP-3α responsive cells may be identified using the reagents described herein. For example, cells which are chemoattracted towards MIP-3α may be purified from other cells by collecting ,those cells which traverse towards MIP-3α. Such chemotaxis may be to a source of chemokine, or may be across a porous membrane or other substrate. See above, in the microchemotaxis assay.

Alternatively, responsive cells may be identified by expression of the receptor, e.g., CCR6, as provided herein. Thus, antibodies which recognize CCR6 may be used as a positive marker for sorting cells likely to respond to MIP-3α. Conversely, the marker may be used to deplete CCR6 bearing cells, e.g., by magnetic depletion or toxic conjugates.

Analysis of human samples can be evaluated in a similar manner. A biological sample, e.g., blood, tissue biopsy sample, lung or nasal lavage, skin punch, is obtained from an individual suffering from a skin related disorder. MIP-3α responsive cell analysis is performed, e.g., by FACS analysis, or similar means.

VIII. MIP-3α Antagonists

Various antagonists of MIP-3α are made available. For example, antibodies against the chemokine itself may block the binding of ligand to its receptor, thereby serving as a direct receptor antagonist. Other antagonists may function by blocking the binding of ligand to receptor, e.g., by binding to the receptor in a way to preclude the possibility of binding of ligand. Other antagonists, e.g., mutein antagonists or aptamers, may bind to the receptor without signaling, thereby blocking a true agonist from binding. Many of these may serve to block the signal transmitted to target cells, specifically MIP-3α-responsive cells. These may be skin cells, including Langerhans, fibroblasts, or keratinocytes.

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

IX. Psoriasis Studies

Psoriasis is a common chronic inflammatory skin disease characterized by a marked inflammatory infiltrate and hyperproliferation of keratinocytes. The infiltrate is composed of skin-infiltrating T cells, predominantly of the memory phenotype, neutrophils, lining macrophages and increased numbers of dendritic cells. Ortonne (1996) *Br. J. Dermatol.* 135:Suppl 49:1–5; Prens, et al. (1995) *Clin. Dermatol.* 13:115–129; and Elder, et al. (1994) *J. Invest. Dermatol.* 102:24S-27S. There is evidence that T cells play a crucial role in the immonopathogenesis of this disease. See, e.g., Gottlieb, et al. (1995) *Nature Med.* 1:442–447; Nicolas, et al. (1991) *Lancet* 338:321; Cooper, et al. (1990) *J. Am. Acad. Dermatol.* 23:1318–1326; Ellis, et al. (1986) *JAMA* 256:3110–3116; Krueger, et al. (1995) *J. Exp. Med.* 182:2057–2068; Schon, et al. (1997) *Nature Med.* 3:183–188; Schon (1999) *J. Invest. Dermatol.* 112:405–410; Wrone-Smith and Nickoloff (1996) [see comments] *J. Clin. Invest.* 98:1878–1887; Uyemura, et al. (1993) *J. Invest. Dermatol.* 101:701–705; (1996) *Arch. Dermatol.* 132:419–423; and Barker (1998) *Hosp. Med.* 59:530–533. An early cellular event in the development of psoriatic lesions is the infiltration of target sites by activated T cells which in turn produce inflammatory mediators, such as IFN-γ, induce epidermal hyperplasia and may act with keratinocytes and dermal macrophages to sustain a cycle of inflammation which finally leads to a psoriatic phenotype. Bata-Csorgo, et al. (1995) *J. Invest. Dermatol.* 105:89S-94S.

A CC chemokine designated macrophage inflammatory protein-3α (MIP-3α; also known as LARC) was previously cloned and characterized, and CCR6 identified as its specific receptor. See, e.g., Rossi, et al. (1997) *J. Immunol.* 158:1033–1036; and Greaves, et al. (1997) *J. Exp. Med.* 186:837–844. MIP-3α is known to attract both T and dendritic cells. See Dieu, et al. (1998) *J. Exp. Med.* 188:373–386; and Power, et al. (1997) *J. Exp. Med.* 186:825–835. Among dendritic cells, MIP-3α is a highly potent chemokine for the chemoattraction of epithelial Langerhans type dendritic cells derived from CD34+ hematopoetic progenitor cells. Dieu, et al. (1998) *J. Exp. Med.* 188:373–386. Recently, MIP-3α has been shown to preferentially attract the memory subset of T cells. Liao, et al. (1999) *J. Immunol.* 162:186–194; and Campbell, et al. (1998) *Science* 279:381–384.

This study sought to identify chemokines and chemokine receptors involved in autoimmune diseases. To this end, an analysis was made of the expression of mRNA of various chemokines and receptors in samples of inflammatory skin diseases using real time quantitative PCR. Here is reported that the expression of the CC chemokine MIP-3α and its receptor CCR6 are significantly upregulated in psoriasis. Within psoriatic lesions, MIP-3α-expressing keratinocytes co-localize with skin-infiltrating T lymphocytes. Furthermore, CCR6 is expressed at high levels on the skin-homing CLA+ subset of memory T cells. Finally, biologically active MIP-3α is induced in cellular constituents of the skin by proinflammatory cytokines and T cell-derived inflammatory mediators. Taken together, these observations strongly suggest that this ligand/receptor pair may represent a unique role in the development of psoriasis.

Patients: 6 mm punch biopsies were taken, after obtaining informed consent, from either lesional. (n=10) and non-lesional (n=5) skin of psoriatic patients or from normal (n=5) healthy individuals. Skin samples were immediately frozen in liquid nitrogen and stored at −80° C. In addition, 50 ml heparinized blood was drawn from either psoriatic patients (n=15) in lesional phases of the disease or healthy donors (n=3) and peripheral blood mononuclear cells were prepared using standard protocols. The psoriatic patients used in this study had been untreated for at least three weeks.

Real Time Quantitative PCR (TaqMan®) Analysis of MIP-3α and CCR6 mRNA Expression: Skin biopsies were homogenized in liquid nitrogen using a Mikro-Dismembrator U (Braun Biotech, San Diego, Calif.) and RNA was extracted with RNAzol according to the manufacturer's protocol (Tel-Test, Friedensburg, Tex.). 4 μg of RNA were treated with DNase I (Boehringer, Mannheim, Germany) and reverse transcribed with oligo $dT_{14-18}$ (Gibco BRL, Gaithersburg, Md.) and random hexamer primers (Promega, Madison, Wis.) using standard protocols. cDNA was diluted to a final concentration of 5 ng/μl. 10 μl of cDNA were amplified in the presence of 12.5 μl of TaqMan® universal master mix (Perkin Elmer, Foster City, Calif.), 0.625 μl of gene-specific TaqMan® probe, 0.5 μl of gene-specific forward and reverse primers, and 0.5 μl of water. As an internal positive control, 0.125 μl of 18S RNA-specific TaqMan® probe and 0.125 μl of 18S RNA-specific forward and reverse primers were added to each reaction. Specific primers and probes for MIP-3α, CCR6, and the other chemokine receptors measured were obtained from Perkin Elmer (Foster City, Calif.). Gene-specific probes used FAM as reporter whereas probes for the internal positive control (18S RNA) were associated with either the JOE or VIC reporters. Samples underwent the following stages: stage 1, 50° C. for 2 minutes; stage 2, 95° C. for 10 minutes; and stage 3, 95° C. for 15 seconds followed by 60° C. for 1 minute. Stage 3 was repeated 40 times. Gene-specific PCR products were measured by means of an ABI PRISM® 7700 Sequence Detection System (Perkin Elmer, Foster City, Calif.) continuously during 40 cycles. Specificity of primer probe combination was confirmed in crossreactivity studies performed against plasmids of all known chemokine receptors (CCR1-CCR9, CXCR1-CXCR5, XCR1, CX3CR1) and the following panel of chemokines: MIP-1α, MIP-1β, MIP-1δ, MIP-3β, 6Ckine, IP-10, Mig, TCA-3, I-309, I-TAC, HCC-1, HCC-4, Gro-α/β, ENA78, eotaxin, eotaxin-2, DC-CK1, BCA-1, fractalkine, SDF-1α, RANTES, PF4, PBP, MDC, lymphotactin, IL-8, TARC, MDC, TECK, and MCP-1-MCP74. Target gene expression was normalized between different samples based on the values of the expression of the internal positive control. Human cDNA libraries used in this study were generated as described previously. See, e.g., Rossi, et al. (1997) *J. Immunol.* 158:1033–1036; Bolin, et al. (1997) *J. Neurosci.* 17:5493–5502; and Vicari, et al. (1997) *Immunity* 7:291–301.

Cell Culture: Human primary epidermal keratinocytes, dermal fibroblasts, melanocytes, and dermal microvascular endothelial cells were purchased from Clonetics (San Diego, Calif.) and cultured in keratinocyte (KGM), fibroblast (FGM), melanocyte (MGM), or endothelial cell (EGM-2) growth medium (Clonetics, San Diego, Calif.) as described in Detmar, et al. (1994) *J. Exp. Med.* 180:1141–1146. Cells were treated with TNF-α (10 ng/ml)/IL-1β (5 ng/ml), IFN-γ (20 ng/ml), IL-4 (50 ng/ml), IL-17 (100 ng/ml) (R&D Systems Inc., Mineapolis, Minn.), or left untreated. The epidermal γδ T cell line, 7-17, was kindly provided by Richard Boismenu (The Scripps Institute, La Jolla, Calif.) and cultured as described previously. See Boilsmenu, et al. (1996) *J. Immunol.* 157:985–992. Epidermal γδ T cells were cultured with Con A, TNF-α (10 ng/ml)/IL-1β (5 ng/ml), or medium alone. Supernatants as well as cells were harvested after 6 or 18 h. Generation of dendritic cells either from cord blood CD34+ hematopoetic progenitor cells or from peripheral blood monocytes was performed as described in Dieu, et al. (1998) *J. Exp. Med.* 188:373–386. Immature dendritic cells from CD34+ hematopoetic progenitor cells or monocyte-derived dendritic cells were activated for 3–24 h in the presence of CD40L transfected L cells (one per five dendritic cells) as described. See Caux, et al. (1994) *J. Exp. Med.* 180:1263–1272. Cells and supernatants were harvested 3, 12, 24, 48 hours after CD40L stimulation. RNA was extracted from cells as described above.

Flow Cytometry and Cell Sorting: In order to analyze chemokine receptor expression of skin-homing T cell subsets, $CLA^+/CD45RO+/CD4+$ cells were sorted from PBMCs isolated from 2 different donor pool buffy coats (70 ml) from 3 individual donors each using a FACS Vantage (Becton Dickinson, San Jose, Calif.) and the following monoclonal antibodies (mAb) (Pharmingen, San Diego, Calif.): FITC-conjugated anti-CLA (HECA4522) mAb, PE-conjugated anti-CD45RO (UCHL1), APC-conjugated anti-CD4 (RPA-T4). The purity of the cells was detected as ≧99.5%., Subsequently, RNA was extracted and reverse transcribed as described above.

In other experiments, CCR6 expression was analyzed on memory T cell subsets using the following antibodies: FITC-conjugated anti-CLA (HECA4522) mAb (Pharmingen, San Diego, Calif.), FITC-conjugated anti-CD45RO (UCHL1) mAb (Pharmingen, San Diego, Calif.), APC-conjugated anti-CD8 (RPA-T8) mAb (Pharmingen, San Diego, Calif.), Cy-chrome-conjugated anti-CD4 (RPA-T4) mAb (Pharmingen, San Diego, Calif.), anti-CCR6-PE conjugated (53103.111) mAb (R&D Systems, Mineapolis, Minn.), mouse $IgG_{2b}$-PE-conjugated (R&D Systems, Mineapolis, Minn.). Briefly, $10^6$ PBMCs were stained with anti-CD4, anti-CD8, anti-CLA, anti-CCR6 mAb or isotype and analyzed using a FACSCalibur and CELLQuest software (Becton Dickinson, San Jose, Calif.).

In Situ Hybridization: In situ hybridization was performed as described. Dieu, et al. (1998) *J. Exp. Med.* 188:373–386. Coupled primers were used for amplifying by RT-PCR the majority of the open reading frame of the MIP-3α gene. +77/MIP-3α forward primer and −425/MIP-3αwere used with an annealing temperature of 62° C. Then, PCR products were cloned into pCRII TA cloning vector (Invitogen, Leek, The Netherlands), RNA probes were synthesized using Sp6 and T7 RNA polymerases (Boehringer Mannheim, Germany) and radiolabled with $^{35}$S-UTP (Amersham Corp., United Kingdom) Sense and anti-sense $^{35}$S-labeled probes of MIP-3α were obtained by run-off transcription of the 367 bp fragment and then partially degraded by alkaline hydrolysis for 20 min at 60° C. 6 µm cryostat sections were prepared on charged electrostatic slides (SuperFrost/Plus, Polylabo, Strasbourg, France) and fixed with cold acetone for 20 min, with 4% paraformaldehyde for 20 min followed by 0.1 M triethanolamine/0.25% acetic anhydride. The sections were hybridized overnight at 50° C. (2 to 3×10$^6$ cpm/slide), RNAse A treated, and exposed for 40 days. After development, the sections were stained with hematoxylin.

Immunohistochemistry: Frozen 6 µm tissue sections were fixed in acetone and in paraformaldehyde before the immunostaining. To block the non-specific binding of avidin, biotin system components, or endogenous peroxidase activity, sections were pre-treated with avidin D and biotin solutions (Blocking kit, Vector, Biosys SA, Compiegne, France) for 10 min each step and with PBS containing 0.3% hydrogen peroxide (Sigma, France) for 15 min at room temperature. After brief washing in PBS, the sections were incubated with blocking serum (2% normal rabbit serum) for at least 30 min before adding both primary antibodies. Sections were double stained simultanously with anti-hMIP-3α goat polyclonal antibody (IgG isotype, R&D Systems Inc., Minesota, Minn.) and anti-hCD3 mouse monoclonal antibody (Leu-4, IgG1 isotype, Becton-Dickinson, Moutain View, Calif.) for 1 hour at room temperature in a humid atmosphere. The binding of goat IgG was detected using biotinylated rabbit anti-goat IgG followed by streptavidin-peroxidase (both included in the Vectastain ABC kit: Goat IgG PK-4005, Vector) and the binding of mouse IgG1 was detected by rabbit alkaline phosphatase-labeled anti-mouse IgG (D0314, Dako, Glostrup, Denmark) at the same time at room temperature in a humid atmosphere. The peroxidase and alkaline phosphatase activities were revealed using 3-amino-9-ethylcarbazole (AEC) substrate (SK-4200, Vector) and alkaline phosphatase substrate III (SK-5300, Vector) for 5 to 10 min at room temperature, respectively. Negative controls were established by adding non-specific isotype controls as primary antibodies.

Generation of Mouse mAbs Against hMIP-3α and Development of an hMIP-3α ELISA: Inbred BALB/c mice were immunized with three successive intraperitoneal injections of complete Freund's adjuvant (Sigma Chemical Co., St. Louis, Mo.), incomplete Freund's adjuvant, or without Freund's adjuvant, respectively, with 50 ng of purified hMIP-3α obtained from supernatants of hMIP-3α transient transfected COP5 cells. Spleens were removed for fusion 3 days after a final i.v. injection of hMIP-3α. Hybridization was carried out using the non-secreting myeloma cell line SP2/0-Ag8 with polyethylene glycol 1000 (Sigma Chemical Co, St. Louis, Mo.). hMIP-3α transient transfected COP5 cells were cultured for 2 days in 96 well plates and fixed in acetone. Then, hybridoma supernatants were harvested after 6 days, were incubated for 30 min on fixed hMIP-3α transient transfected COP5 cells. Antibody binding was then revealed with peroxidase-conjugated sheep anti-mouse IgG (Biosys, Compiegne, France) at a 1:200 dilution in PBS for 30 min at 37° C. Positive hybridomas were cloned by limiting dilution and expanded using a high density culture system (Integra cell line CL1000, Integra Biosciences, France). After sodium sulphate precipitation, the mAbs were purified by anion-exchange chromatography on a Hyper-D column and peroxidase labeled (Sepracor, Villeneuve, France). An ELISA was set up using one of the anti-hMIP-3α mAbs, 319F6, as a capture mAb and a peroxidase-coupled mouse anti-hMIP-3α mAb to reveal the captured hMIP-3α. The assay proved to be specific for MIP-3α with a sensitivity of 0.2 ng/ml.

Analysis of hMIP-3α bioactivity by calcium mobilization assay: A cell line expressing the human CCR6 chemokine receptor was kindly provided by Chuan Chu Chou (SPRI, Kennilworth, N.J.). Briefly, the CCR6 open reading frame was cloned into the pME18sneo eukaryotic expression vector and transfected into the murine B-cell line, BAF/3 by electroporation. Stable transfectants were isolated by selection in medium containing 1 mg/ml G418. CCR6 expression was confirmed using calcium signaling, ligand binding analysis with recombinant human MIP-3α (R&D Systems, Minneapolis, Minn.), and immunohistochemistry with anti-CCR6 (53103.111) mAb (R&D Systems, Minneapolis, Minn.). The average number of binding sites per cell was estimated to be 220, 000.

To measure the biological activity of the MIP-3α produced by keratinocytes fibroblast or endothelial cells, supernatants from these cell cultures were concentrated 20-fold using Centriplus concentrators with a cut off of 3 kD (Amicon, Beverly, Mass.). The calcium response to supernatants from these resting or activated cells was measured using standard protocols. See, e.g., Greaves, et al. (1997) *J. Exp. Med.* 186:837–844. Briefly, the BAF/3 parental and CCR6 transfectant were loaded for 60 min at 37° C. with 3 µM INDO-1A (Molecular Probes, Eugene, Oreg.). Cells were washed and resuspended in Hank's balanced salt solution (HBSS) (Gibco/BRL, Grand Island, N.Y.) to a final concentration of 10$^7$ cells/ml. Calcium mobilization was measured using a Photon, Technology International spectrophotometer with excitation at 350 nm and dual simultaneous recording of fluorescence emission at 400 nm and 490 nm. Relative intracellular calcium levels are expressed as the 400 nm/490 nm emission ratio. Experiments were performed at 37° C. with constant mixing in cuvettes containing 10$^6$ cells in 2 ml of HBSS with 1 mM CaCl$_2$. In order to demonstrate specificity of MIP-3α-induced calcium mobilization, neutralization studies were performed using a blocking mouse anti-human MIP-3α. (IgG1) (67310.111) mAb (R&D Sytems, Minneapolis, Mo.) or isotype control (IgG$_1$) (Sigma, St. Louis Mo.).

MIP-3α and its Specific Receptor CCR6 Are Significantly Upregulated in Lesional Psoriatic Versus Non-Lesional or Normal Skin: After cloning and initial characterization of mouse and human MIP-3α and identification of its receptor, CCR6, the potential role of this ligand-receptor pair was investigated in human diseases. See Rossi, et al. (1997) *J. Immunol.* 158:1033–1636; and Greaves, et al. (1997) *J. Exp. Med.* 186:837–844. To this end, a systematic screening of human tissue cDNA libraries with MIP-3α- and CCR6-specific TaqMan® probe and primers was undertaken. The cDNA library panel included various libraries derived from human autoimmune disease samples. This initial screening showed that MIP-3αwas expressed more than 100-times higher in a cDNA library derived from lesional psoriatic skin (568000 fg/50 ng cDNA) when compared to normal skin (5530 fg/50 ng cDNA). Moreover, TaqMan® analyses showed abundant CCR6 message (864 fg/50 ng cDNA) in the cDNA library generated from psoriatic skin. In contrast, CCR6 was undetectable in a cDNA library derived from normal skin. Other chemokine receptors that have been reported to be upregulated in psoriasis were investigated in the cDNA libraries from normal and psoriatic skin. To this end, the expression of the IL-8 receptors was studied, and confirmed previous reports. See Kulke, et al. (1998) *J.*

Invest. Dermatol. 110:90–94; and Schulz, et al. (1993) J. Immunol. 151:4399–4406. CXCR1 and CXCR2 were constitutively expressed in the cDNA library derived from normal skin and markedly upregulated in the psoriatic skin cDNA library. Thus, the cDNA libraries derived from normal or psoriatic skin provided representative tools to study gene expression. These initial observations prompted investigation of a possible role for MIP-3α and CCR6 in the pathogenesis of psoriasis in more detail. These led to efforts to validate these observations in more patient samples. Consecutive quantitative real time PCR analysis of cDNA derived from either lesional (n=10), non-lesional (n=5) psoriatic or normal (n=5) skin confirmed that both MIP-3α and CCR6 were significantly upregulated in lesional psoriatic versus non-lesional or normal skin (P<0.005). An average 7- and 4-fold induction of MIP-3α and CCR6 could be detected, respectively. To look more precisely at the distribution of MIP-3α, in situ hybridization and immunohistochemistry were performed using specific probes and polyclonal antibodies directed against MIP-3α. In situ hybridization with a MIP-3α specific probe showed selective expression of this chemokine in the suprabasal layers of the epidermis of lesional psoriatic skin. These showed specific hybridization within the stratum granulosum of lesional psoriatic skin. In addition, MIP-3α mRNA expression could be detected within the stratum spinosum of psoriatic epidermis. Sense (vs antisense) controls as well as in situ hybridization with normal and non-lesional psoriatic skin confirmed the specific detection of MIP-3α hybridization in lesional psoriatic skin. Furthermore, immunohistochemical staining of lesional psoriatic skin confirmed the focal upregulation of MIP-3α protein within suprabasal layers of the epidermis. In contrast, non-lesional psoriatic and normal skin showed no specific staining for MIP-3α. Staining with isotype controls showed the specificity of MIP-3α detection. Attempts to detect CCR6 by immunohistochemistry for CCR6 were inconclusive due to the low sensitivity of the antibody. Therefore, double stainings were performed for MIP-3α and CD3 to study localization of MIP-3α-expressing cells and T cells. Immunohistochemisty of lesional psoriatic skin showed that focal accumulation of T cells in the papillary dermis of lesional psoriatic skin was directly adjacent to foci of MIP-3α-expressing epidermal cells. Moreover, MIP-3α-expressing keratinocytes within the epidermis co-localized with intraepidermal $CD3^+$ T cells.

Peripheral Blood Mononuclear Cells From Psoriasis Patients Express Significantly Higher Levels of CCR6 When Compared With Those of Healthy Donors: Clinically, it is well known that infections may trigger psoriatic episodes and recently it has been suggested that superantigens may play a role in T cell activation during the pathogenesis of psoriasis. See Valdimarsson, et al. (1997) Clin. Exp. Immunol. 107 Suppl 1:21; Nickoloff, et al. (1993) J. Immunol. 150:2148–2159; and Nickoloff, et al. (1993) J. Dermatol. Sci. 6:127–133. However, very little is known about chemokine receptor expression on PBMCs of normal healthy donors versus psoriatic patients. Interestingly, CCR6 was also significantly upregulated in PBMCs derived from psoriasis patients (n=10) versus PBMC from healthy donors (n=5) (P<0.001). PBMCs from psoriatic patients expressed on average:4-fold higher levels of CCR6 mRNA when compared with PBMCs from healthy donors. The CLA+ T cell subset represents a skin-associated population of memory T cells that migrates preferentially to normal and chronically inflamed cutaneous sites. See Picker, et al. (1990) J. Immunol. 145:3247–3255.

Subsequent experiments focused on the chemokine receptor profile of pathologically relevant skin-homing $CLA^+$ memory T cells. Flow cytometric analyses revealed that CCR6 was expressed at high levels on the surface of skin-homing $CLA^+$ T cells of normal donors. Moreover, CCR6 was predominantly expressed on the $CD4^+$ subset of $CLA^+$ T cells. The latter observation may account for the therapeutic effect of anti-human CD4 antibodies in the treatment of psoriasis. See Isaacs, et al. (1997) Clin. Exp. Immunol. 110:158≧166; Thivolet and Nicolas (1994) Int. J. Dermatol. 33:327–332; and Morel, et al. (1992) J. Autoimmun. 5:465–477.

In agreement with flow cytometric analyses, TaqMan® analyses on sorted CLA+ memory T cells from normal donors indicated that they express CCR6 at high levels. In fact, the expression of CCR6 was the highest one detected among chemokine receptors, especially when compared to receptors of other chemokines (IL-8, Gro-α, IP-10, Mig, MCP-1, RANTES) that have already been associated with psoriasis. See Schulz, et al. (1993) J. Immunol. 151:4399–4406; Gottlieb, et al. (1988) J. Exp. Med. 168:941–948; Lemster, et al. (1995) Clin. Exp. Immunol. 99:148–154; Gillitzer, et al. (1993) J. Invest. Dermatol. 101:127–131; Fukuoka, et al. (1998) Br. J. Dermatol. 138:63–70; and Goebeler, et al. (1998) J. Pathol. 184:89–95. CCR6 expression was 100 to more than 1000-times higher than CXCR1, CXCR2, CXCR3, CCR2, CCR3 and CCR5 on this skin-homing subset of memory T cells.

TNF-α, IL-1β, IFN-γ, IL-17, and CD40L Regulate the Expression of MIP-3α in Cellular Constituents of the Skin: The pattern of MIP-3α expression within the epidermis suggested that keratinocytes may be a major source for MIP-3α in the skin. To further investigate the cellular origin of MIP-3α within the skin and to get insights into its regulation, human primary keratinocytes, melanocytes, and dermal fibroblasts were cultured with TNF-α/IL-1β, IFN-γ, IL-4, IL-17, or medium alone as control. Furthermore, it was tested whether cultured epidermal γδ T cells resting or stimulated with either TNF-α/IL-1β or Con A may express MIP-3α. Human primary dermal microvascular endothelial cells were also cultured in the presence or absence of TNF-α/IL-1β. TNF-α and IL-1β were used for stimulation since these proinflammatory cytokines are known to be upregulated during inflammatory conditions and in psoriatic lesional skin. See Terajima, et al. (1998) Arch. Dermatol. Res. 290:246–252; Mizutani, et al. (1997) i J. Dermatol. Sci. 14:145–153; Debets, et al. (1995) Eur. J. Immunol. 25:1624–1630; Nickoloff, et al. (1991) Am. J. Pathol. 138:129–140; and Gomi, et al. (1991) [see comments] Arch. Dermatol. 127:827–830. Furthermore, the effects of T helper cell-derived cytokines such as IL-4, IFN-γ, and IL-17 were tested on cellular constituents of the skin. TaqMan® analyses showed that only keratinocytes and dermal microvascular endothelial cells constitutively express low levels of MIP-3α and that TNF-α/IL1β can induce MIP-3α mRNA expression in both keratinocytes and dermal microvascular endothelial cells. In addition, TNF-α/IL-1 β stimulation of dermal microvascular endothelial cells induced strong upregulation of MIP-3α expression. Activation of both CD34+ hematopoetic progenitor cell- or monocyre-derived dendritic cells with CD40L also induced MIP-3α-specific transcripts. Interestingly, melanocyces also showed significant expression of MIP-3α following TNF-α/IL-1β stimulation. Moreover, MIP-3α expression could be markedly induced in these cells by IFN-γ or IL-4 stimulation. Keratinocytes showed a weak (2–4 fold) upregulation of MIP-3α mRNA after activation with either IFN-γ or IL-4. In contrast, resting or stimulated epidermal γδ T cells failed to express MIP-3α mRNA under any conditions. Similar results were observed in keratinocytes (n=4), melanocytes (n=2), CD34+ hematopoietic progenitor cell-derived dendritic cells (n=2), monocyte-derived dendritic cells (n=2), dermal microvascular endothelial cells (n=2) and dermal fibroblasts (n=2) of different donors. Interestingly, keratinocytes, fibroblasts, melanocytes, or epidermal γδ T cells were never observed to express significant levels of CCR6 mRNA.

Analyses of MIP-3α protein expression by ELISA confirmed that activated keratinocytes, dermal microvascular endothelial cells, dermal fibroblasts, and monocyte-derived dendritic cells are potent producers of this chemokine. Supernatants from cultured primary human keratinocytes, dermal microvascular endothelial cells, and dermal fibroblasts activated with TNF-α and IL-1β showed a marked induction of MIP-3α protein while resting cells showed either little or no production of MIP-3α. These levels of hMIP-3α production are in the range of biological activity reported for prokaryote-derived recombinant hMIP-3α. Low levels of MIP-3α protein were also detected after stimulation of keratinocytes with IFN-γ or IL-17, however, additional TNF-α stimulation showed synergistic effects and markedly enhanced MIP-3α protein production.

Supernatants of monocyte-derived dendritic cells showed significant production of MIP-3α protein (1.14–8.76 ng/ml) 12 to 48 h following CD40L stimulation. MIP-3α protein expression generally confirmed the data obtained using real time quantitative PCR (TaqMan®). However, supernatants from CD34+ hemacopoetic progenitor cells stimulated with CD40L did not contain detectable MIP-3α protein despite a marked induction of MIP-3α mRNA expression. This may be due to the high level of CCR6 expression by these cells suggesting that they may be binding and internalizing MIP-3α.

It was then sought to determine if the MIP-3α protein detected in these supernatants was biologically active. To this end, supernatants were tested against keratinocytes, fibrobasts, or endothelial cells, either resting or following stimulation with TNF-α/IL-1β, IFN-γ, IL-4, in a calcium signaling assay using CCR6-transfected BAF/3 cells. These cells are known to express endogenous CXCR4. Therefore, to obtain a CCR6-specific assay, the endogenous CXCR4 was blocked with human SDF-1α prior to testing the supernatants for MIP3α activity. In agreement with the ELISA data, supernatants from keratinocytes, dermal fibroblasts, and dermal microvascular endothelial cells stimulated with TNF-α/IL-1β induced significant calcium mobilization responses in CCR6-transfected BAF/3 cells but not in the parental untransfected BAF/3 cells. However, the parental BAF/3 cell line showed the expected calcium mobilization response due to the triggering of endogenous CXCR4 by SDF-1α. Furthermore, treatment with anti-MIP-3α mAb completely neutralized supernatant-induced calcium mobilization in CCR6-transfected BAF/3 cells, however, isotype control showed no effect. Concentrated medium with or without cytokine (TNF-α/IL-1β, IL-4, IFN-γ) addition did not produce any intracellular Ca++ mobilization in parental or CCR6-transfected cells. These results confirm the production of bioactive MIP-3αprotein by keratinocytes, dermal fibroblasts, and dermal microvascular endothelial cells initially detected at the mRNA level by quantitative PCR.

This study demonstrates that the CC chemokine MIP-3α and its receptor CCR6 are significantly upregulated in psoriasis. Furthermore, clusters of skin-infiltrating T cells in the papillary dermis of lesional psoriatic skin are directly adjacent to foci of MIP-3α-expressing epidermal cells. Moreover, MIP-3α-expressing keratinocytes within the epidermis co-localize with intraepidermal $CD3^+$ T cells. These findings together with the observation of Liao, et al. (1999) *J. Immunol.* 162:186–194 that MIP-3α specifically attracts the memory subset of T cells in vitro strongly suggests that MIP-3α plays an important role in T cell recruitment to lesional psoriatic skin. The significantly increased expression of CCR6 in PBMCs derived from psoriatic donors and the high expression of CCR6 on skin-homing $CLA^+$ T cells further supports this concept. In addition to memory T cells, peripheral blood B cells also express CCR6, however, they are not present in psoriatic skin lesions (Bata-Csorgo, et al. (1995) *J. Invest. Dermatol.* 105:89S–94S; Liao, et al. (1999) *J. Immunol.* 162:186–194; Bos, et al. (1983) *Arch. Dermatol. Res.* 275:181–189; and Bos, et al. (1989) *Arch. Dermatol. Res.* 281:24–30) suggesting that there may be further necessary requirements such as E-selectin or CLA expression for effective skin homing. The CLA+ T cell subset represents a skin-associated population of memory T cells that preferentially extravasates to normal and chronically inflamed cutaneous sites. See Picker, et al. (1990) *J. Immunol.* 145:3247–3255. Comparison of CCR6 expression in CLA+ T cells with those of receptors for chemokines (IL-8, Gro-α, IP-10, MIC, MCP-1, RANTES) reported to be associated with psoriasis underscore the relevance of this specific chemokine/receptor pair in psoriasis. Schulz, et al. (1993) *J. Immunol.* 151:4399–4406; Gottlieb, et al. (1988) *J. Exp. Med.* 168:941–948; Lemster, et al. (1995) *Clin. Exp. Immunol.* 99:148–154; Gillitzer, et al. (1993) *J. Invest. Dermatol.* 101:127–131; Fukuoka, et al. (1998) *Br. J. Dermatol.* 138:63–70; and Goebeler, et al. (1998) *J. Pathol.* 184:89–95. Furthermore, the predominance of CCR6 expression on the CD4 subset of skin-homing CLA+ T cells suggests a link with the effective treatment of psoriasis using anti-human CD4 antibodies. See Isaacs, et al. (1997) *Clin. Exp. Immunol.* 110:158–166; Thivolet and Nicolas (1994) *Int. J. Dermatol.* 33:327–332; and Morel, et al. (1992) *J. Autoimmun.* 5:465–477. These findings support previous observations by Campbell, et al. (1998) *Science* 279:381–384 showing that MIP-30α induces rapid adhesion to ICAM-1 only in memory but not in naive CD4+ T cells. Furthermore, immunohistological studies have shown that the inflammatory infiltrate in psoriasis is mainly composed of CD4+ memory T cells. See Prens, et al. (1995) *Clin. Dermatol.* 13:115–129; and Bata-Csorgo, et al. (1995) *J. Invest. Dermatol.* 105,:89S–94S.

Interestingly, TaqMan(D analyses of cDNA libraries show that CCR6 is predominantly expressed in cDNA libraries derived from human $Th_0$ or $Th_1$ clones. However, cDNA libraries derived from either activated $Th_2$ polarized cells or resting or activated $Th_2$ (HY935) clones show little or no CCR6 expression. This expression pattern supports previous observations indicating that lesional psoriatic T cells predominantly display a $Th_1$ phenotype. See Uyemura, et al. (1993) *J. Invest. Dermatol.* 101:701–705; Barker (1998) *Hosp. Med.* 59:530–533; Nestle, et al. (1994) *J. Clin. Invest.* 94:202–209; and Schlaak, et al. (1994) *J. Invest. Dermatol.* 102:145–149. In addition, preliminary experiments show that activated T cells are capable of inducing high levels of MIP-3α production in epithelial cells.

Keratinocytes are potent producers of MIP-3α in lesional psoriatic skin. Here it is shown that TNF-α and IL-1, both proinflammatory cytokines known to be upregulated in psoriasis, (see Terajima, et al. (1998) *Arch. Dermatol. Res.* 290:246–252; Mizutani, et al. (1997) *J. Dermatol. Sci.* 14:145–153; Debets, et al. (1995) *Eur. J. Immunol.* 25:1624–1630; Nickoloff, et al. (1991) *Am. J. Pathol.*

138:129–140; and Gomi, et al. (1991) [see comments] *Arch. Dermatol.* 127:827–830) as well as CD40L are potent inducers of bioactive MIP-3α protein in keratinocyces, melanocytes, dermal microvascular endothelial cells, dermal fibroblast, and dendritic cells in vitro. Furthermore, T helper cell-derived mediators (e.g., IFN-γ, IL-17, CD40L) regulate MIP-3α production in cellular constituents of the skin. IL-17 is known to be upregulated in lesional psoriatic skin, suggesting that it may play a role in the amplification and the development of cutaneous inflammation. See Nestle, et al. (1994) *J. Clin. Invest.* 94:202–209; and Teunisseh, et al. (1998) *J. Invest. Dermatol.* 111:645–649. Here it is shown that it is another inducer of MIP-3α protein production by primary keratinocytes.

In vitro epithelial Langerhans-type dendritic cells can be generated from CD34+ hematopoietic progenitor cells, however, monocyte-derived dendritic cells share phenotypic characteristics with dermal dendritic cells. It has been reported previously that CCR6 is highly expressed on dendritic cells derived from CD34+ hematopoetic progenitor cells and that MIP-3α selectively induces migratory responses in CD34+ hematopoetic progenitor cell—but not in monocyte-derived dendritic cells. See Greaves, et al. (1997) *J. Exp. Med.* 186:837–844; and Dieu, et al. (1998) *J. Exp. Med.* 188:373–386. In lesional psoriatic skin, large numbers of dermal dendritic cells are present and show potent stimulatory functions. Nestle, et al. (1994) *J. Clin. Invest.* 94:202–209. Activation of dendritic cells via CD40 triggering resulted in a marked upregulation of MIP-3α suggesting that dendritic cell-T lymphocyte interactions may amplify inflammatory processes in psoriasis.

In summary, these data suggest that T cell-derived mediators, such as CD40L, IFN-γ, and IL-17, may amplify chemokine, particularly MIP-3α, production in lesional psoriatic skin and may contribute to the development and/or chronicity of psoriatic lesions. Thus, blockage of effect may be therapeutically effective, e.g., by use of antagonists, receptor, antagonists, or receptor desensitization compounds.

Along with its expression in intestinal epithelial cells, cutaneous MIP-3α expression supports the hypothesis that this inflammatory chemokine plays an important role in the interface between the organism and the environment. Tanaka, et al. (1999) *Eur. J. Immunol.* 29:633–642. Other chemokines have been shown to be associated with psoriasis, including RANTES which has been reported to be expressed in psoriatic lesions by activated keratinocytes. See Fukuoka, et al. (1998) *Br. J. Dermatol.* 138:63–70; and Raychaudhuri, et al. (1999) *Acta Derm. Venereol.* 79:9–11. However, peak levels of RANTES expression (2.072 ng/ml) in activated keratinocytes were 10–50 times lower than those detected for MIP-3α in the present study. Fukuoka, et al. (1998) *Br. J. Dermatol.* 138:63–70. Furthermore, there is divergent data regarding RANTES expression in lesional psoriatic skin. Fukuoka, et al. (n=3) as well as Raychaudhuri, et al. (n=8) reported increased RANTES expression in lesional psoriatic skin using immunohistochemistry in a total of 11 psoriatic patients, whereas Goebler, et al. reported no detectable RANTES expression in either lesional psoriatic (n=11), non-lesional psoriatic (n=11), or normal skin (n=5). Goebeler, et al. (1998) *J. Pathol.* 184:89–95. The present study observed markedly lower levels of RANTES expression in a cDNA library derived from psoriatic skin when compared with one derived from normal skin using RANTES-specific primers and probes for real time quantitative PCR (TaqMan®) analyses. In contrast to RANTES, Goebler, et al. detect strong selective expression of Mig in the upper lesional dermis with pronounced clustering in the tips of the papillae, whereas expression in normal or non-lesional psoriatic or normal skin was quiescent. Co-localization studies have suggested that highly activated dermal macrophages and dermal microvascular endothelial cells are major sources of Mig in lesional psoriatic skin. Goebeler, et al. (1998) *J. Pathol.* 184:89–95. The pro-inflammatory CC chemokines, IP-10 and Mig, are able to attract activated T cells and are mainly regulated by T cell-derived cytokines, such as IFN-γ. Thus, skin-infiltrating activated T cells release inflammatory mediators which, in turn, induce Mig, IP-10, and MIP-3α, contributing to the amplification of inflammatory responses and to the chronicity of psoriatic lesions. Moreover, MCP-1 expression of keratinocytes in the stratum basale of lesional psoriatic skin is associated with chemoattraction of dermal macrophages to lesional sites. See Gillitzer, et al. (1993) *J. Invest. Dermatol.* 101:127–131; Goebeler, et al. (1998) *J. Pathol.* 184:89–95; and Deleuran, et al. (1996) *J. Dermatol. Sci.* 13:228–236.

Given the cumulating evidence that psoriasis is a T-cell mediated disease, MIP-3α/CCR6 is the first ligand/receptor pair identified in this disease which is directly associated with memory T cell recruitment to lesional psoriatic skin. The only other chemokine/receptor pairs reported in psoriasis, such as IL-8 and GRO-α with their receptors CXCR1 and CXCR2, are mainly involved in the recruitment of neutrophils to lesional psoriatic skin. See Gillitzer, et al. (1996) *J. Invest. Dermatol.* 107:778–782; Gillitzer, et al. (1991) *J. Invest. Dermatol.* 97:73–79; and Kulke, et al. (1996) *J. Invest. Dermatol.* 106:526–530. In addition, the expression pattern of those CXC chemokines did not fully coincide with the pattern of T cell accumulation. See Gillitzer, et al. (1996) *J. Invest. Dermatol.* 107:778–782; Gillitzer, et al. (1991) *J. Invest. Dermatol.* 97:73–79; and Kulke, et al. (1996) *J. Invest. Dermatol.* 106:526–530.

Recently, Campbell, et al. suggested that the interaction of the CC chemokine TARC with its receptor CCR4 plays an important role in the homing of memory T cells to the skin. Campbell, et al. (1999) *Nature* 400:776–780. TARC expression was shown to be exclusively expressed in endothelial cells of both normal and inflamed human skin and this CC chemokine could induce firm adhesion and chemotaxis of skin-homing memory T cells. Taken together, these findings suggest that TARC and CCR4 may play a role in the interaction of skin-homing T cells with the dermal endothelium and transendothelial migration, however, other chemokines (e.g., MIP-3α, IP-10, Mig) expressed by keratinocytes, fibroblasts, or dendritic cells may mediate the localization of skin-homing T cells to the dermis and epidermis. MIP-3α has also been shown to mediate firm adhesion of CD4+ memory T cells suggesting that chemokines may also act in an orchestrated fashion at this particular step of leukocyte trafficking.

Most recently, a non-chemokine ligand for CCR6 has been identified. Yang, et al. showed that human β-defensin-2 is able to bind CCR6 transfected cells and to induce chemotaxis, however, its chemotactic activity was considerably lower than that of MIP-3α. Yang, et al. (1999) [In Process Citation] *Science* 286:525–528. Interestingly, like MIP-3α, human β-defensin-2 is upregulated by proinflammatory mediators, such as TNF-α and IL-1β. Most importantly, bacterial and viral infections markedly induce the production of human β-defensin-2. Since both MIP-3α and human β-defensin-2 are expressed in psoriatic skin, they could both contribute to the recruitment of memory T cells to lesional sites, however, these studies found no evidence for a role for human β-defensin-2 since the intracellular Ca$^{2+}$ mobilization induced by supernatants of TNF-α/IL-1β-stimulated primary keratinocytes in CCR6 transfectants was completely blocked by an anti-MIP-3α antibody.

These findings suggest the following model for the involvement of MIP-3α and CCR6 in the pathogenesis of psoriasis: MIP-3α may, be induced in keratinocytes and/or dermal microvascular endothelial cells at sites of physical injury or infection due to the release of proinflammatory cytokines, such as TNF-α and IL-1. In turn, TARC and MIP-3α may induce adhesion (Campbell, et al. (1998) *Science* 279:381–384; and Campbell, et al. (1999) *Nature* 400:776–780) and chemotaxis of skin-homing memory T cells (Liao, et al. (1999) *J. Immunol.* 162:186–194) through the endothelium into the skin. Subsequently, the skin-homing CLA+ T cells may encounter their specific antigen presented by dendritic cells, get activated, and produce inflammatory mediators, such as IFN-γ, IL-17, or CD40L, which, in turn, induce additional MIP-3α, IP-10, and Mig production by activated keratinocytes, dendritic cells, and dermal macrophages. Gottlieb, et al. (1988) *J. Exp. Med.* 168:941–948; Goebeler, et al. (1998) *J. Pathol.* 184:89–95; and Boorsma, et al. (1998) *Arch. Dermatol. Res.* 290:335–341. This "second wave" of chemokine production may complete a self-sustaining cycle of inflammation which leads to the development of a psoriatic phenotype.

In conclusion, this study shows the potential that a highly specific and sensitive real time quantitative PCR technique (TaqMan®) offers to identify novel disease associations with the expression of specific genes. This technology led to the identification of MIP-3α/CCR6 as a new ligand/receptor pair potentially involved in the pathogenesis of psoriasis.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed:

1. A method for modulating migration of a lymphoid cell or a myeloid cell within or to the skin of a mammal suffering from inflammation, said method comprising administering to said mammal an effective amount of an antibody to MIP-3α, wherein said MIP-3α is a polypeptide comprising the amino acid sequence set forth in SEQ ID NO: 2, SEQ ID NO: 4, or SEQ ID NO: 6, each of said amino acid sequences being without a signal sequence, whereby administration of said antibody ameliorates inflammation.

2. The method of claim 1, wherein said migration is within said skin.

3. The method of claim 2, wherein said migration is chemotactic or chemokinetic.

4. The method of claim 1, wherein said administering is systemic, local, topical, subcutaneous, intracutaneous, or transdermal.

5. The method of claim 1, wherein said lymphoid cell is a B cell.

6. The method of claim 1, wherein said lymphoid cell is a T cell.

7. The method of claim 1, wherein said lymphoid cell or said myeloid cell migrates into the dermal and/or epidermal layers of said skin.

8. The method of claim 1, wherein said antibody is administered in combination with an analgesic.

9. The method of claim 1, wherein said antibody is administered in combination with an anti-inflammatory drug.

10. The method of claim 1, wherein said myeloid cell is a dendritic cell.

11. The method of claim 1, wherein said myeloid cell is a dendritic cell precursor.

12. The method of claim 1, wherein said antibody is administered in combination with an antibiotic.

13. The method of claim 1, wherein said antibody is administered in combination with an antifungal agent.

14. The method of claim 1, wherein said antibody is administered in combination with an antiviral agent.

15. The method of claim 1, wherein said antibody is administered in combination with an immune suppressive therapeutic.

16. The method of claim 1, wherein said antibody is administered in combination with a growth factor.

17. The method of claim 1, wherein said antibody is administered in combination with an immune adjuvant.

18. The method of claim 1, wherein said antibody neutralizes MIP-3α.

19. The method of claim 1, wherein said inflammation is caused by psoriasis.

20. The method of claim 1, wherein said inflammation is caused by a microbial or a parasitic infection.

21. The method of claim 1, wherein said inflammation is caused by skin transplant.

22. The method of claim 1, wherein said inflammation is caused by skin graft.

* * * * *